(12) United States Patent
Oshida et al.

(10) Patent No.: US 7,309,568 B2
(45) Date of Patent: Dec. 18, 2007

(54) METHOD IN INSPECTING DNA AND APPARATUS THEREFOR

(75) Inventors: Yoshitada Oshida, Chigasaki (JP); Satoshi Takahashi, Hitachinaka (JP); Kenji Yasuda, Tokyo (JP); Taisaku Seino, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 471 days.

(21) Appl. No.: 10/229,204

(22) Filed: Aug. 26, 2002

(65) Prior Publication Data
US 2003/0087282 A1 May 8, 2003

(30) Foreign Application Priority Data
Sep. 26, 2001 (JP) ............................. 2001-292783
Feb. 13, 2002 (JP) ............................. 2002-034805

(51) Int. Cl.
*C12Q 1/68* (2006.01)
*C12M 1/00* (2006.01)
*B32B 5/02* (2006.01)
*G01N 21/00* (2006.01)

(52) U.S. Cl. ................. 435/6; 435/283.1; 435/288.7; 422/82.05; 422/82.07

(58) Field of Classification Search .................... None
See application file for complete search history.

(56) References Cited

U.S. PATENT DOCUMENTS

| 5,495,105 | A | * | 2/1996 | Nishimura et al. ......... 250/251 |
| 5,684,565 | A | * | 11/1997 | Oshida et al. ............... 355/53 |
| 5,776,674 | A | * | 7/1998 | Ulmer .......................... 435/6 |
| 6,136,543 | A | * | 10/2000 | Anazawa et al. .............. 435/6 |
| 6,288,220 | B1 | * | 9/2001 | Kambara et al. ......... 536/24.31 |
| 6,355,921 | B1 | | 3/2002 | Staton et al. |
| 6,518,556 | B2 | | 2/2003 | Staton et al. |
| 6,759,235 | B2 | * | 7/2004 | Empedocles et al. .... 435/288.7 |

FOREIGN PATENT DOCUMENTS

| JP | 2001-208688 A | 8/2001 |
| JP | 2002-005834 A | 1/2002 |

* cited by examiner

*Primary Examiner*—BJ Forman
(74) *Attorney, Agent, or Firm*—Townsend and Townsend and Crew LLP

(57) ABSTRACT

A method and apparatus of stably obtaining fluorescent images of two or more fluorescent samples includes disposing the samples onto compartments defined on a substrate. The compartments are sequentially irradiated with an exciting light where the intensity varies. A value of fluorescence as generated from each of the samples is determined, and a fluorescent image is obtained based on the value of fluorescence.

18 Claims, 22 Drawing Sheets

METHOD IN INSPECTING DNA AND APPARATUS THEREFOR

BACKGROUND OF THE INVENTION (1) Field of the Invention

The present invention relates to a method of obtaining a fluorescent image, and an apparatus for carrying out the method; and a method of detecting a fluorescence-labeled DNA so as to inspect the DNA, and an apparatus for carrying out the method.

Furthermore, the present invention relates to a method of detecting or inspecting a matter which emits fluoresce by itself, or a fluorescence-labeled matter, in particular, a fluorescence-labeled DNA, and an apparatus for carrying out the method. Particularly, the present invention relates to a high-speed method of detecting or inspecting a fluorescent material as arranged in the form of a bead-array or a dot-array with high sensitivity and in a wide dynamic range, and an apparatus for carrying out the method.

(2) Description of the Related Art

An apparatus for shifting a position to be dotted on a glass substrate by means of a spotter according to the type of a probe DNA; and/or an apparatus for reading the intensity of fluorescence of samples which are provided by hybridizing a fluorescence-labeled probe DNA with what is called a DNA micro-array as obtained according to a photolithography technology have been employed in this field. With such an apparatus, a procedure comprising the steps of: irradiating a fluorescence-labeled probe DNA with an exciting laser spot beam having a certain fixed intensity, detecting a fluorescent light as generated from the probe DNA by means of a photo-multiplier, and determining the intensity of fluorescence from the detected signal is sequentially carried out for all the samples.

When such an apparatus is used for the expression and/or analysis of a DNA in tissue, whose object is to inspect the DNA, the ratio of concentration between target mRNAs or between target cDNAs which are the copies of the mRNAs may be larger than 1:10,000. Even in such a case, in order to precisely detect the targets, it is very important to detect the same in a wide dynamic range.

However, the prior method of detection mentioned above has, for example, the problem that it is not easy to detect the same in a wide dynamic range, and furthermore remarkably much time is required.

In addition, conventionally, as a method of detecting samples wherein fluorescent materials or fluorescence-labeled DNAs are arranged in the form of a bead array or a dot array, a method comprising the steps of: forming an exciting laser light into one spot, relatively scanning samples with the exciting laser spot light, and detecting the resultant fluorescent lights has been used. Besides, a method comprising the steps of: area-irradiating the wide area of a sample with an exciting light, and detecting the resultant fluorescent lights by means of a two-dimensional CCD or the like.

When the one spot light mentioned above is irradiated so as to relatively scan the samples with the exciting laser spot light for detection, since samples in the form of bead or dot array are scanned all over the surface thereof, the rate of time as substantially and effectively used for detecting fluorescent lights is very small as explained below. That is to say, when the diameter of a bead or dot is represented by "D", and the pitch between the beads or dots is represented by "P", if the array is in the form of an in-line arrangement, the rate of time as effectively used for detecting fluorescent lights during the scanning is $\pi D^2/4P^2$. Then, for example, if the ratio of D to P is 1:2, the rate of time is 19.6%, and even if the ratio is 1:1.5, the rate of time is 34.9%, which means that more than a half of the time is not effectively used for detection.

Furthermore, since one spot light is irradiated for detection, when samples consist of a lot of beads or dots, much time is required for detecting fluorescent lights. Therefore it is difficult to detect fluorescent lights at a high speed. In addition, when it is intended to detect fluorescent lights with high sensitivity and in a wide dynamic range, since time for exciting one bead or dot is to some extent required, the sensitivity and the dynamic range have to be sacrificed for achieving high-speed detection.

Similarly, when the area-irradiation and the two-dimensional detection are employed as mentioned above, the above-mentioned useless time is required, and thus the dynamic range have to be sacrificed for achieving high-speed detection.

SUMMARY OF THE INVENTION

The present invention provides a method of obtaining fluorescent images, whereby even the fluorescent images of samples having a 10,000 times or more concentration-difference between the same can be stably detected in a wide dynamic range with high resistivity at a high speed; and an apparatus for carrying out the same.

Furthermore, the present invention provides a method of inspecting a DNA whereby a fluorescence-labeled probe DNA can be stably detected in a wide dynamic range at a high speed with high resistivity; and an apparatus for carrying out the same.

That is to say, the present invention provides a method of obtaining fluorescent images of two or more samples which may includes a fluorescent material, comprising the steps of:

(a) disposing each of said samples onto each of two or more compartments which an area on a substrate is split into;

(b) sequentially irradiating said compartments with an exciting light wherein each of said compartments is irradiated with said exciting light with the intensity changed;

(c) detecting one or more fluorescent lights as generated from each of said samples corresponding to said changed intensity of said exciting light every each of said samples; and (d) determining the true value of fluorescence as generated from each of said samples by using information on said one or more fluorescent lights as detected every each of said samples.

Furthermore, the present invention provides a method of determining the values of fluorescence as generated from samples which may include a fluorescent material, comprising the steps of:

(a) arraying said samples on an area on a substrate;

(b) sequentially irradiating said samples with one or more exciting lights wherein each of said samples is irradiated with said one or more exciting lights;

(c) obtaining two or more fluorescent images of each of said samples with two or more fluorescent lights different in intensity from one another as generated from each of said samples by the irradiation with said one or more exciting lights in said irradiating step (b); and (d) treating said two or more fluorescent images of each of said samples as obtained in said obtaining step (c) so as to determine the true value of fluorescence as generated from each of said samples.

Besides, the present invention provides an apparatus for obtaining fluorescent images of two or more samples which may include a fluorescent material, comprising:

(A) an exciting-lights generating means for generating two or more exciting lights different in intensity from one another;

(B) an exciting-lights irradiating means for sequentially irradiating each of said samples with said two or more exciting lights as generated by means of said exciting-lights generating means, with the intensity switched, so as to sequentially irradiating said samples with said two or more exciting lights;

(C) a fluorescent-lights detecting means for detecting two or more fluorescent lights as generated from each of said samples corresponding to said two or more exciting lights different in intensity from one another by sequentially irradiating each of said samples with said two or more exciting lights by means of said exciting-lights irradiating means;

(D) a treating means for treating said two or more fluorescent lights as generated from each of said samples corresponding to said two or more exciting lights different in intensity from one another so as to obtain information on said two or more fluorescent lights as generated from each of said samples; and (E) an obtaining means for obtaining a fluorescent image of each of said samples by using said information on said two or more fluorescent lights.

Furthermore, the present invention provides a method of inspecting DNAs, comprising the steps of:

(a) adding a fluorescence-label to DNAs so as to prepare p (wherein p represents an integer, $p \geq 2$) of DNA-samples;

(b) disposing each of said p of DNA-samples upon each of p' (wherein p' represents an integer, $p' \geq p \geq 2$) of compartments which an area on a substrate is divided into;

(c) irradiating each of said p of DNA-samples with one of q (wherein q represents an integer, $q \geq 1$) of exciting lights, wherein with each of said q of exciting lights switched into r (wherein r represents an integer, $r \geq 2$) of beams different in intensity from one another, each of said p of DNA-samples is sequentially irradiated with said r of beams;

(d) detecting r of fluorescent lights as generated from each of said p of DNA-samples in said irradiating step (c), corresponding to said r of beams different in intensity from one another; and (e) inspecting a DNA in each of said p of DNA-samples by using information upon said r of fluorescent lights as detected in said detecting step (d).

The present invention also provides a method of inspecting DNAs, comprising the steps of:

(a) adding a fluorescence-label to DNAs so as to prepare p (wherein p represents an integer, $p \geq 2$) of DNA-samples;

(b) disposing each of said p of DNA-samples upon each of p' (wherein p' represents an integer, $p' \geq p \geq 2$) of compartments which an area on a substrate is divided into;

(c) irradiating each of said p of DNA-samples with one of q (wherein q represents an integer, $q \geq 1$) of exciting lights, wherein with each of said q of exciting lights switched into two beams different in intensity from each other, each of said p of DNA-samples is sequentially irradiated with said two beams;

(d) converging two fluorescent lights as generated from each of said p of DNA-samples in said irradiating step (c), corresponding to said two beams different in intensity from each other;

(e) branching said two fluorescent lights as converged in said converging step (d) into two fluorescent lights different in intensity from each other so as to detect each of said branched two fluorescent lights; and (f) inspecting a DNA in each of said p of DNA-samples by using information upon each of said two fluorescent lights as detected in said detecting step (e).

The present invention also provides a method of inspecting DNAs, comprising the steps of:

(a) adding a fluorescence-label to DNAs so as to prepare p (wherein p represents an integer, $p \geq 2$) of DNA-samples;

(b) attaching each of said p of DNA-samples to the surface of each of p' (wherein p' represents an integer, $p' \geq p \geq 2$) of beads or dots as arrayed at a certain fixed pitch on a bead- or dot-array on a substrate;

(c) continuously moving said p of DNA-samples in one direction;

(d) irradiating each of said p' of beads or dots with one spot of a spot exciting-light comprising q (wherein q represents an integer, $q \geq 1$) of spots, each of said q of spots having the diameter of a beam approximately equal to the diameter of each of said beads or dots, wherein said p' of beads or dots which are continuously travelling in one direction are irradiated with said spot exciting-light so that said spot exciting-light can track said beads or dots, so that a period of time as required for moving each spot by said certain fixed pitch can be almost used for irradiating each of said beads or dots;

(e) separating fluorescence as generated from each of said p of DNA-samples from said spot exciting-light so as to detect said fluorescence; and (f) inspecting said DNAs by using information as obtained in said detecting step (e).

The present invention also provides a method of inspecting DNAs, comprising the steps of:

(a) adding a fluorescence-label to DNAs so as to prepare p (wherein p represents an integer, $p \geq 2$) of DNA-samples;

(b) attaching each of said p of DNA-samples to the surface of each of p' (wherein p' represents an integer, $p' \geq p \geq 2$) of beads as arrayed at a certain fixed pitch on a substrate;

(c) moving said p' of beads in one direction, pitch by pitch;

(d) irradiating each of said p' of beads with one spot of q (wherein q represents an integer, $q \geq 1$) of exciting-lights, each of said q of exciting-lights having the diameter of a beam approximately equal to the diameter of each of said beads, wherein q (wherein $p \geq q \geq 1$) of said beads are irradiated with said q of exciting-lights while said p' of beads which step-travel are stopping;

(e) separating fluorescence as generated from each of said p of DNA-samples from said q of exciting-lights so as to detect said fluorescence; and (f) inspecting said DNAs by using information as obtained in said detecting step (e).

Furthermore, the present invention provides an apparatus for inspecting DNAs, comprising:

(A) an exciting-light generating means for generating one or more exciting lights;

(B) an exciting-light irradiating means for sequentially irradiating each of two or more DNA-samples with each of said two or more exciting lights as generated by means of said exciting light generating means, with two or more beams switched different in intensity from one another, wherein a fluorescent label is added to each of said two or more DNA-samples, and each of said two or more DNA-samples is disposed on each of two or more compartments upon a substrate; and said DNA-samples being sequentially irradiated with said one or more exciting lights;

(C) a fluorescent-lights detecting means for detecting two or more fluorescent lights as generated from each of said DNA-samples, corresponding to said two or more beams switched different in intensity from one another by sequentially irradiating each of said DNA-samples with each of said one or more exciting lights, with two or more beams switched different in intensity from one another; and (D) a treating means for treating two or more signals for detecting fluorescence as detected according to said two or more beams different in intensity from one another, switched by said fluorescence detecting means so that information upon fluorescence as generated from each of said two or more beams can be obtained.

The present invention also provides an apparatus for inspecting DNAs, comprising:

(A) an exciting-light generating means for generating q (wherein q represents an integer, q≧1) of exciting lights;

(B) an exciting-light irradiating means for irradiating each of p (wherein p represents an integer, p≧2) of DNA-samples with one of said q of exciting lights, wherein a fluorescent label is added to each of said p of DNA-samples, and each of said p of DNA-samples is disposed on each of p' (wherein p' represents an integer, p'≧p≧2) of compartments upon a substrate;

(C) a fluorescent-lights converging and branching means for converging r (wherein r represents an integer, r≧1) of fluorescent lights as generated from each of said p of DNA-samples by the irradiation with said exciting-light irradiating means, and branching said converged fluorescent lights into s (wherein s represents an integer, s≧2) of fluorescent lights;

(D) a fluorescent-lights detecting means for detecting each of said branched s of fluorescent lights; and (E) a fluorescent-image obtaining means for obtaining fluorescent images of said detected s of fluorescent lights; and (F) a treating means for treating said fluorescent images as obtained by said fluorescent-image obtaining means (E) so as to obtain information upon fluorescence as generated from each of said p of DNA-samples.

In order to detect fluorescence in the method of detecting fluorescence as explained above, when a photon counting method is employed wherein each of photons is detected, a higher-sensitive and wider dynamic-range detection can be achieved.

When the above-mentioned means is employed, letting a pulse width of the signal of photon count pulses be "ΔT", and letting a period of time for detecting photons count for one picture element be "T", the detection with a dynamic range of 0.5·T/ΔT or more can be achieved, whereby the detection with a dynamic range of 1000 or more, or even 10000 or more can be achieved.

Furthermore, according to the present invention, in order to solve the problem mentioned above, the following means are employed.

First of all, each of samples are irradiated with exciting lights in the form of spots each of which has the diameter of a beam approximately equal to the diameter of a bead or a dot in a bead-array or a dot-array, onto which a fluorescent material in each of the samples is attached. The bead- or dot-array and the exciting lights in the form of spots relatively travel, the resultant scanned fluorescent lights are separated from the exciting lights and detected. In this case, each of the exciting lights in the form of spots is operated to home on each of the arrayed beads or dots so that the bead- or dot-array can be substantially continuously irradiated with the exciting lights in the form of spots within a period of time required for relatively scanning one pitch between the arrayed beads or dots, whereby almost all the period of scanning can be utilized for detecting fluorescence, which has not been achieved in the prior art.

Furthermore, in order to obtain a similar advantageous effect, when fluorescence is detected by relatively moving a bead- or dot-array and exciting lights in the form of spots so as to scan samples, the bead- or dot-array wherein each of the samples including fluorescence is disposed on each of beads or dots is step-moved by one pitch step so that the bead- or dot-array can be substantially continuously irradiated with the exciting lights in the form of spots within a period of time required for relatively scanning one pitch between the arrayed beads or dots.

Besides, the exciting lights in the form of spots shall be in the form a multispot, whereby samples on a lot of beads or dots can be simultaneously detected. As a result, the high-sensitive, wider dynamic-range and high-speed detection of fluorescence can be achieved.

According to the present invention, in order to ensure the detection mentioned above, the deviation of a scanning direction in the light distribution when a spot exciting light is reflected from a bead or dot or diffracted therethrough is detected, and on the basis of the signal of the detection, the position of the spot exciting light and the position of the sample are corrected.

Furthermore, the deviation of a tracking direction in the light distribution when the spot exciting light is reflected from the bead or dot or diffracted therethrough is detected. On the basis of the signal of the detection, the position of the spot exciting light or the position of the sample in the fluorescent bead- or dot-array is corrected in a direction orthogonal to the direction of the array of the bead- or dot-array. In such a manner, consequently, the beads or dots can be substantially normally irradiated with the exciting light with precision.

Furthermore, as the method of detecting fluorescence as mentioned above, a photon counting method for detection may be employed, whereby not only a period of time for the above-mentioned detection can be increased, but also even samples generating weak fluorescent lights on beads or dots can be detected with high sensitivity at a high speed.

In addition, according to the present invention, within a period of time required for relatively scanning the arrayed beads or dots mentioned above by one pitch, the intensity of the exciting light may be changed in some phases so that fluorescence in each of the phases can be separated and detected, whereby even when some samples generate strong fluorescent lights, and others generate weak fluorescent lights, both samples can be detected with high precision at high speed in a wider dynamic-range.

These and other objects, and the features and advantageous effects of the present invention will be clarified by a detailed description of the following preferred embodiments of the present invention with reference to the accompanying drawings.

DESCRIPTION OF THE PREFERRED EMBODIMENTS

The present invention will be in detail explained with the working examples as follows.

First of all, a high-speed and high-sensitive method of inspecting a DNA in a wide dynamic range of the present invention, and an apparatus therefor will be explained with FIGS. 1 to 10.

A first working example wherein a DNA is inspected with a wide dynamic range, with high sensitivity and at high speed will be explained with reference to FIGS. 1 to 4.

Figure 1:
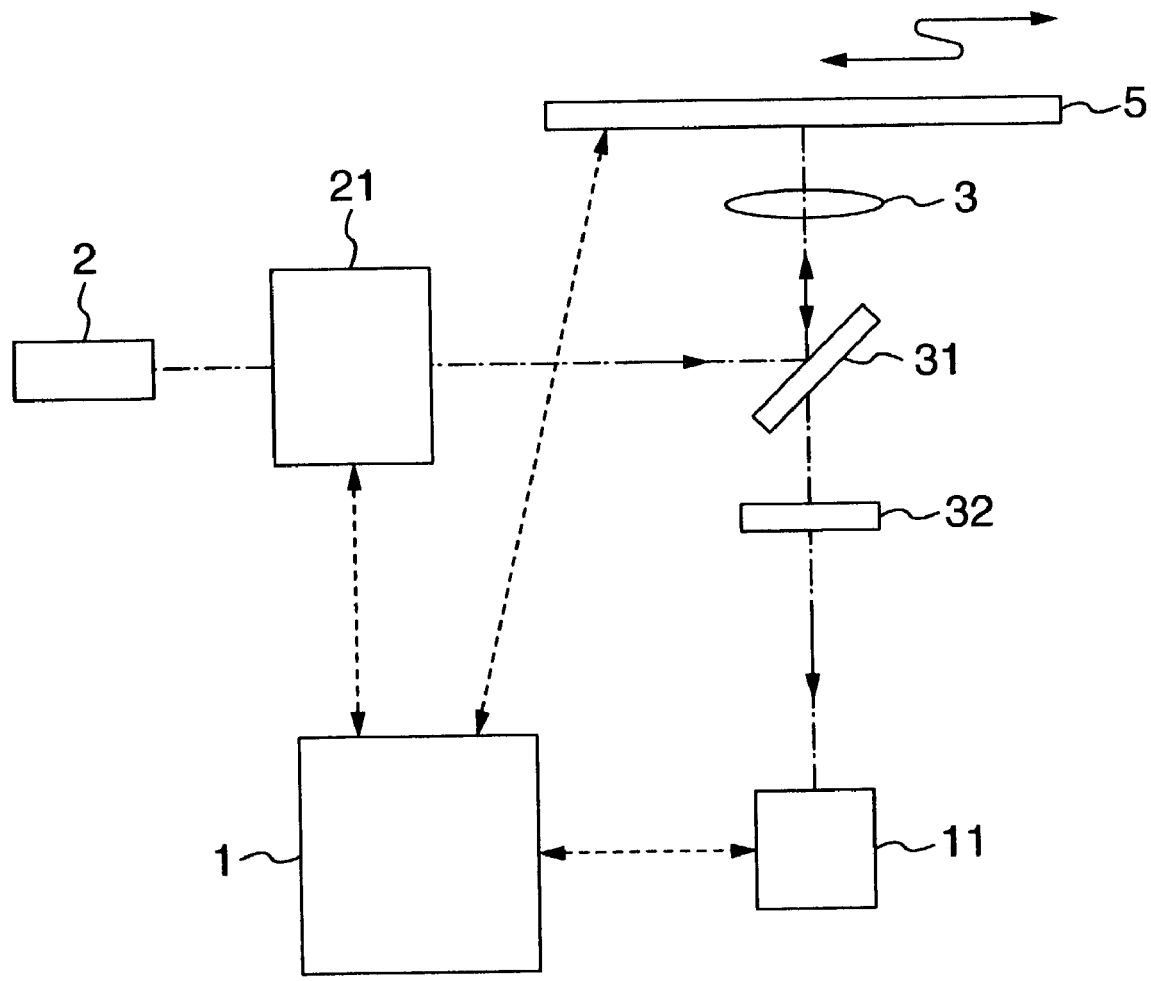
FIG. 1 is a front view illustrating a schematic structure of a first working example of an apparatus for inspecting a DNA according to the present invention.

In FIG. 1, the reference numeral "2" represents an exciting light source for generating an exciting light having a wavelength of $\lambda 1$. A beam of light emitted from the exciting light source is formed into a laser beam by means of an exciting light beam forming optical system (21) so that a desired form of beam can be provided onto a sample (5) through an object lens (3). The formed exciting light beam to be irradiated onto the sample is preferably a multiple-spot beam, or may be an one-spot beam. A wavelengths-selecting beam splitter (31) is disposed between the exciting light beam forming optical system (21) and the object lens (3) in the way of the exciting light path. The beam splitter (31) for selecting wavelengths reflects the exciting light beam having a wavelength of $\lambda 1$ from the forming optical system (21) for exciting light, while a fluorescent light having a wavelength of $\lambda 2$ as emitted from a fluorescent material as carried by the sample (5) is transmitted.

Specifically, when "Cy 3", which is the name of an Amersham Pharmacia Biotech K. K.—made product, is used and the second harmonic laser from YAG is used as an exciting light, the wavelength $\lambda 1$ is 532 nm, and the peak value of fluorescence wavelengths $\lambda 2$ is 570 nm. Thus the wavelength-selecting mirror (31) reflects a wavelength of 532 nm in a ratio of 90% or more, while transmits fluorescence wavelengths of from 560 to 590 nm in a ratio of about 90%. The fluorescence waveband mentioned above of the transmitted fluorescent light is transmitted through an influence filter (32), while the exciting light having a wavelength of 532 nm as leaked from the wavelength-selecting mirror (31) is almost completely light-shielded.

The fluorescent light as transmitted through the influence filter (32) is detected by means of a high-sensitive detector (11) such as a photo-multiplier. A photon count pulse signal as detected by means of the high-sensitive detector (11) is fed to a control circuit (1), and converted into digital information, and then saved in memory together with positional information on the sample from which photon has been generated. In the present working example, an example wherein a photo-multiplier is used as the fluorescence detector has been explained: a semiconductor detector such as a cooled CCD may be used. Furthermore, excited spots may be irradiated over a wide area so as to be detected as a two-dimensional image by means of the cooled CCD.

Figure 2A:
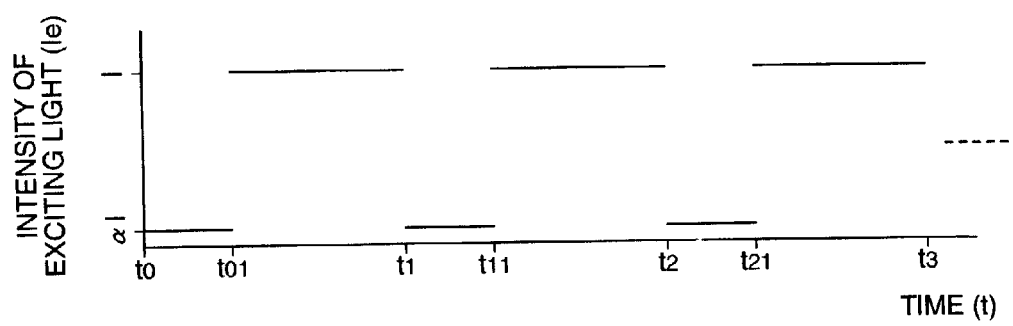
FIG. 2A is a graph demonstrating the change of the intensity of an exciting light with time in the present invention.

The control circuit (1) performs a function to change the intensity of an exciting light. That is to say, for example, as shown in FIG. 2A, the intensity of an exciting laser can be changed with time by using an AO-modulator (acoustic-optic modulator). In the present working example, an exciting laser irradiates the surface of the sample by the diameter of a beam corresponding to the size of one picture-element to be detected on the sample. As shown in FIG. 1, the sample (5) is scanned in an X-direction within the surface of the sample with a stage (not shown) on the basis of a control signal from the control circuit (1).

Figure 2B:
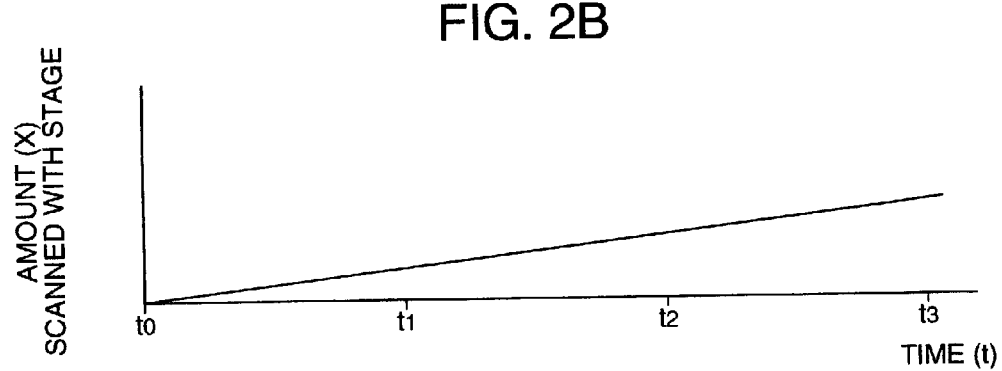
FIG. 2B is a graph demonstrating the change of the amount of stage-scanning with time in the present invention.

FIG. 2B demonstrates the relationship between the variation of time taken for this stage-scanning and the position of the sample. The scale of the abscissa axis of FIG. 2A is the same as that of FIG. 2B, wherein one picture element is scanned between the time "$t_0$" and the time "$t_1$", and a fluorescence intensity of the one picture element is detected during this time. A period of time between the time "$t_0$" and the time "$t_1$" is divided into two time zones; one is a period of time between the time "$t_0$" and the time "$t_{01}$", and the other is a period of time between the time "$t_{01}$" and the time "$t_1$". As shown in FIG. 2A, an exciting light with weak intensity ($\alpha$I) is irradiated during the former period of time, while an exciting light intensity (I) is irradiated during the latter period of time. Thereafter, an adjacent picture element is detected through the stage-scanning, while a period of time between the time "$t_1$" and the time "$t_2$," is divided into two time zones; one is a period of time between the time "$t_1$," and the time "$t_{11}$", and the other is a period of time between the time "$t_{11}$", and the time "$t_2$". As shown in FIG. 2A, an exciting light with weak intensity ($\alpha$I) is irradiated during the former period of time, while an exciting light intensity (I) is irradiated during the latter period of time in a similar manner thereto.

Figure 3:
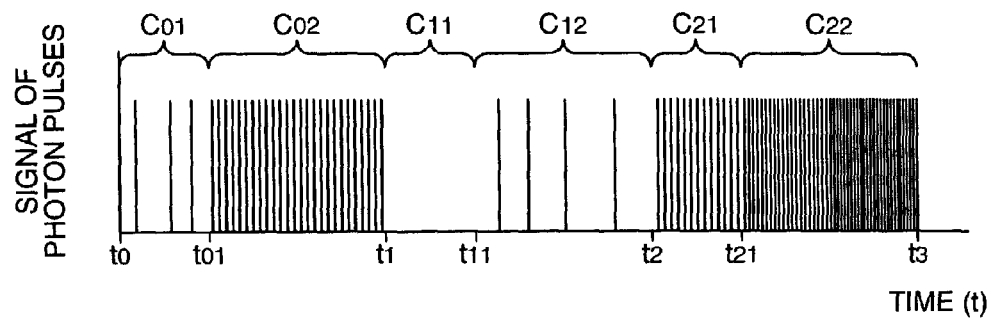
FIG. 3 is a diagram demonstrating the signal of photon pulses count in the present invention.
Figure 4:
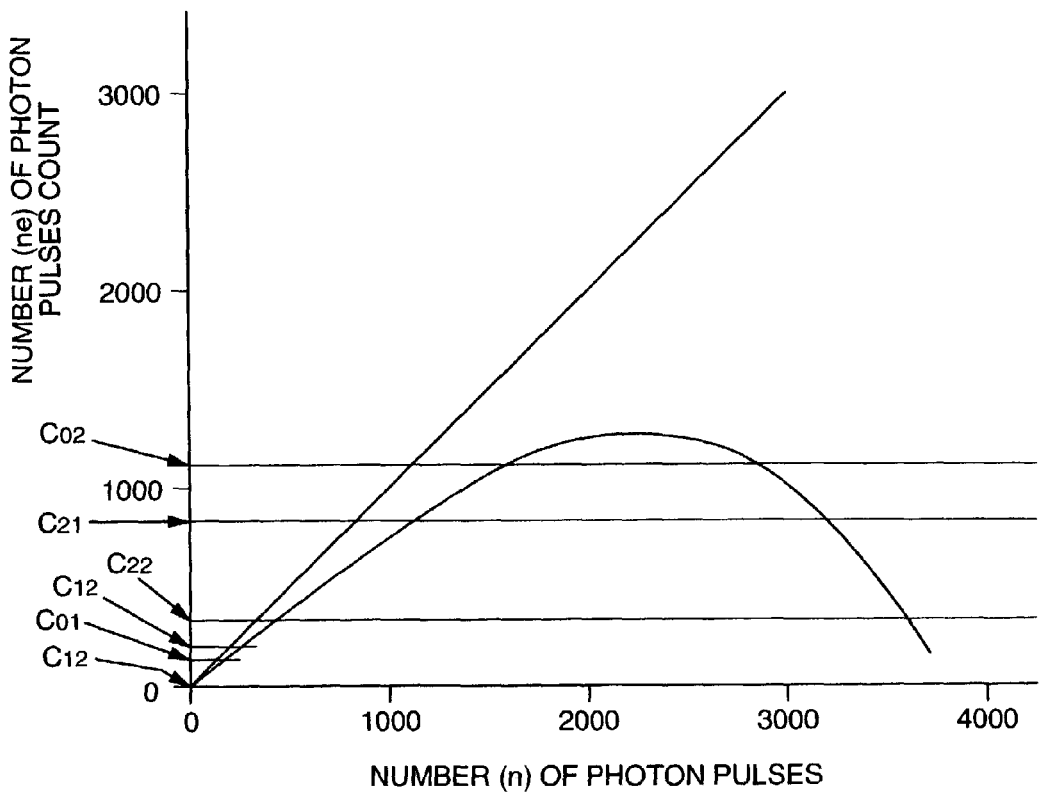
FIG. 4 is a diagram demonstrating the relationship between the signal of photon pulses and the number of photon pulses count in the present invention.

Thus the intensity of an exciting light is changed during one picture element is scanned with the beam of an exciting light, whereby the detection of a fluorescent light in a wide dynamic range can be attained as shown in FIGS. 3 and 4. FIG. 3 exemplifies the result of the detection of fluorescence according to a photon counting method when an exciting light beam has passed through three picture elements, which demonstrates that with respect to the concentration of fluorescence labels in each of the sequential three picture elements, the concentration between the time "$t_0$" and the time "$t_1$" is of a common level, the concentration between the time "$t_1$" and the time "$t_2$" is of a very low level, and the concentration between the time "$t_2$" and the time "$t_3$" is of a very high level. Since the concentration between the time "$t_0$" and the time "$t_1$" is common and the intensity ($\alpha$I) of the exciting light between the time "$t_0$" and the time "$t_{01}$" is weak, the photon pulse signal is sparse, and thus the number ($C_{01}$) of the photon pulses count is a small value. On the other hand, the intensity (I) of the exciting light between the time "$t_{01}$" and the time "$t_1$" is strong and nearly saturated but not saturated, and thus the number ($C_{02}$) of the photon pulses count a large value.

In FIG. 4, the intensity of detected fluorescence is taken as the abscissa axis, and the number of the photon pulses count is taken as the vertical axis. When the intensity of detected fluorescence is strong, adjacent photon pulses are superposed upon each other, whereby the number of photon pulses count is apparently decreased. Therefore, as exemplified in FIG. 4, when the number of photons come into the detector is on the order of 2300, the number of photon pulses count is maximized, while when the number of photons come into the detector is more largely increased as compared to the above number, the number of photon pulses count is conversely decreased. Therefore, the number of photon pulses count between the time "$t_{01}$" and the time "$t_1$" results in a level as indicated by the arrow of $C_{02}$ in FIG. 4, wherein two candidate values exist for the true number of photon pulses therebetween, but it remains to be seen which candidate value is true.

However, if the value of the number $C_{01}$ of photon pulses count between the time "$t_0$" and the time "$t_{01}$" prior to this detection, which is detected through an exciting light with weak intensity ($\alpha$I), can be seen, it can be seen which candidate value of the two values mentioned above is true. When the value of $C_{02}$ is smaller than a predetermined value, the employment of a true value as selected from the two candidate values which have been detected with an exciting light with strong intensity (I) provides a result with rather higher precision. Thus the true value as detected with an exciting light with strong intensity (I) should be employed. Conversely, when the value of $C_{02}$ is larger than the predetermined value, the value as detected with the exciting light with weak intensity ($\alpha$I) should be preferably employed. Nevertheless, as shown in FIG. 4, since the graph is not linear, the true correction value of the number of photon pulses is calculated according to the after-mentioned correction method.

The density of fluorescence labels in a picture-element as detected over a period of time between the following time "$t_1$" and the time "$t_2$" in FIG. 3 is very small. Therefore, when the intensity of an exciting light is $\alpha$I, the number of photon pulses count is zero. On the other hand, when the intensity of an exciting light is "I", the value of $C_{12}$ is detectable, which is small. In this case as well, the value of $C_{12}$ as detected with an exciting light with strong intensity is used to calculate the true correction value of the number of photon pulses.

The density of fluorescence labels in a picture-element as detected between the following time "$t_2$" and the time "$t_3$" is very large. Thus even an exciting light with weak intensity ($\alpha$I) can satisfactorily provide the number $C_{21}$ of photon pulses count. Conversely, when the intensity of an exciting light is "I", photon pulses are superposed upon each other, whereby the number $C_{22}$ of photon pulses count is smaller rather than the number $C_{21}$. Like this, when the number $C_{22}$ of photon pulses count with an exciting light with strong intensity (I) is smaller than the number $C_{21}$ of photon pulses count with an exciting light with weak intensity ($\alpha$I), the number $C_{21}$ of photon pulses count should be employed.

Both the number of photon pulses count on an exciting light with weak intensity and the number thereof on an exciting light with strong intensity, as explained hereinbefore, are recorded in memories in the control circuit (1), and either or both of the two numbers is (are) used to calculate the true correction value of the number of photon pulses. Incidentally, although the photon counting method is employed in the working example mentioned above, even when an analog detection is employed as a method of detecting fluorescence, exciting lights different from each other in intensity are used so that a more precise fluorescence detection can be achieved in a wide dynamic range. Nevertheless, according to the photon counting method, even a weaker fluorescent light can be detected. Thus when a high-sensitive detection is necessary, it is more advantageous to employ the photon counting method.

Furthermore, when the diameter of an exciting light to be irradiated to the sample is narrowed down to a size corresponding to the size of a picture element into a spot-light, and this spot-light and samples are relatively scanned so as to carry out a scanning and detection all over the samples, it is advantageous to employ a multiple spot-light in order to realize the speeding-up of detection. When the number of the spots of the multiple spot-light is represented as "M", and even if the time required for detecting all of the samples is presumed to be "the time required for detecting one picture element" multiplied by, for example, $\sqrt{M}$, the time required for detecting one picture element can be decreased to $1/\sqrt{M}$. When the number of photon pulses count is detected, the effect of the dynamic range being widened in proportion to the time taken for detecting one picture element can be provided. Thus the longer the time is taken for detection, the wider the dynamic range for detection can be.

A second working example wherein a DNA is inspected with a wide dynamic range and high sensitivity at a high speed will be explained with reference to FIG. 5.

Figure 5:
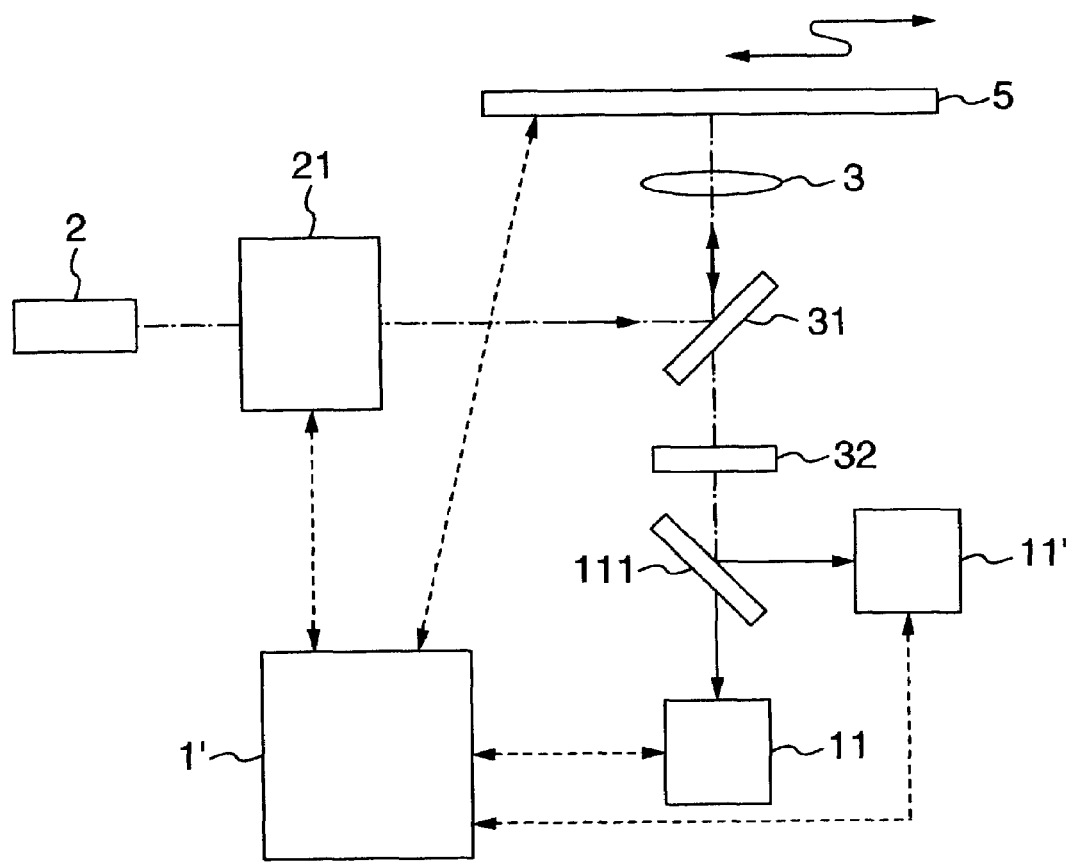
FIG. 5 is a front view illustrating a schematic structure of a second working example of an apparatus for inspecting a DNA according to the present invention.

The basic constitution of FIG. 5 is the same as the one shown in FIG. 1, and thus the same reference numeral as the one in FIG. 1 indicates the same element as the one in FIG. 1. A constant strong exciting light is irradiated to a sample (5), which is different from the step in the working example as illustrated in FIG. 1. An emitted fluorescent light is sequentially transmitted through an object lens (3), a first beam splitter (31) for selecting wavelengths, and an influence filter (32), and thereafter it comes into a second beam splitter (111). The second beam splitter (111) reflects the emitted fluorescent light in a ratio of 95%, while transmits the same in a ratio of 5%. After the transmission and reflection of the emitted fluorescent light, the emitted fluorescent light is detected by first and second photo-multipliers (11 and 11'), whereby the second photo-multiplier (11') detecting the emitted fluorescent light in a ratio of 5% can detect about the same detection value as the value as detected with a weak exciting light in the working example illustrated in FIG. 1 mentioned above, while the first photo-multiplier (11) detecting the emitted fluorescent light in a ratio of 95% can detect about the same detection value as the value as detected with a strong exciting light therein. As a result, the results detected by both the first and the second photo-multipliers (11 and 11') are fed to a control circuit (1') and stored therein, in a similar manner to the one in the working example illustrated in FIG. 1, and these two detected results are used, whereby the high-precision detection of fluorescence can be achieved in a wide dynamic range in a similar manner to the one mentioned above.

Although in this system it is necessary to use the two photo-multipliers, it is not necessary to control the strength of the exciting light, and it is not necessary to time-share the exciting light and to alternate the strength and the weakness for detection. Therefore a time for detection can be taken approximately two times so as to detect the number of photon pulses count, and thus the dynamic range can be widened by just that much.

When the pulse width of a photon pulse signal is represented by $\Delta T$, and "the time $(t_{n+1}-t_n)$ of photon pulses count for one picture element as shown in FIGS. 2A and 2B and FIG. 3" $=T$, wherein n is an integral number, according to a conventional method, a dynamic range as shown in FIG. 4 is less than $0.5 \cdot T/\Delta T$, while the employment of a system of the present invention as demonstrated in FIGS. 1 or 5 can provide the detection of the number of photon pulses count in a dynamic range of $0.5 \cdot T/\Delta T$ or more for the first time. Specifically, according to a conventional method it was difficult to provide a value of 1,000 or more: however, according to a method of the present invention a value of 1,000 or more can be provided.

Furthermore, according to the present invention, an exciting light having two or more phases in intensity is employed in, or a fluorescent light to be detected is branched into first and second fluorescent lights, and the ratio of the intensity of the first branched fluorescent light to the intensity of the second fluorescent light from 1:dozens to 1:several hundred is provided, and then these fluorescent lights are in parallel detected, whereby the dynamic range mentioned above can be increased to 10,000 or more for the first time.

In addition, according to the present invention, even an extremely weak fluorescent light can be detected by the employment of the photon counting method mentioned above; the dynamic range mentioned above can be satisfied; and the number of photon pulses count can be detected with fluorescence-detection sensitivity of the number of fluorescent molecules of 50 or less per one picture element. Furthermore, the dynamic range mentioned above can be satisfied; and the number of photon pulses count can be detected with fluorescence-detection sensitivity of the number of fluorescent molecules of 10 or less per $mm^2$.

Figure 6:
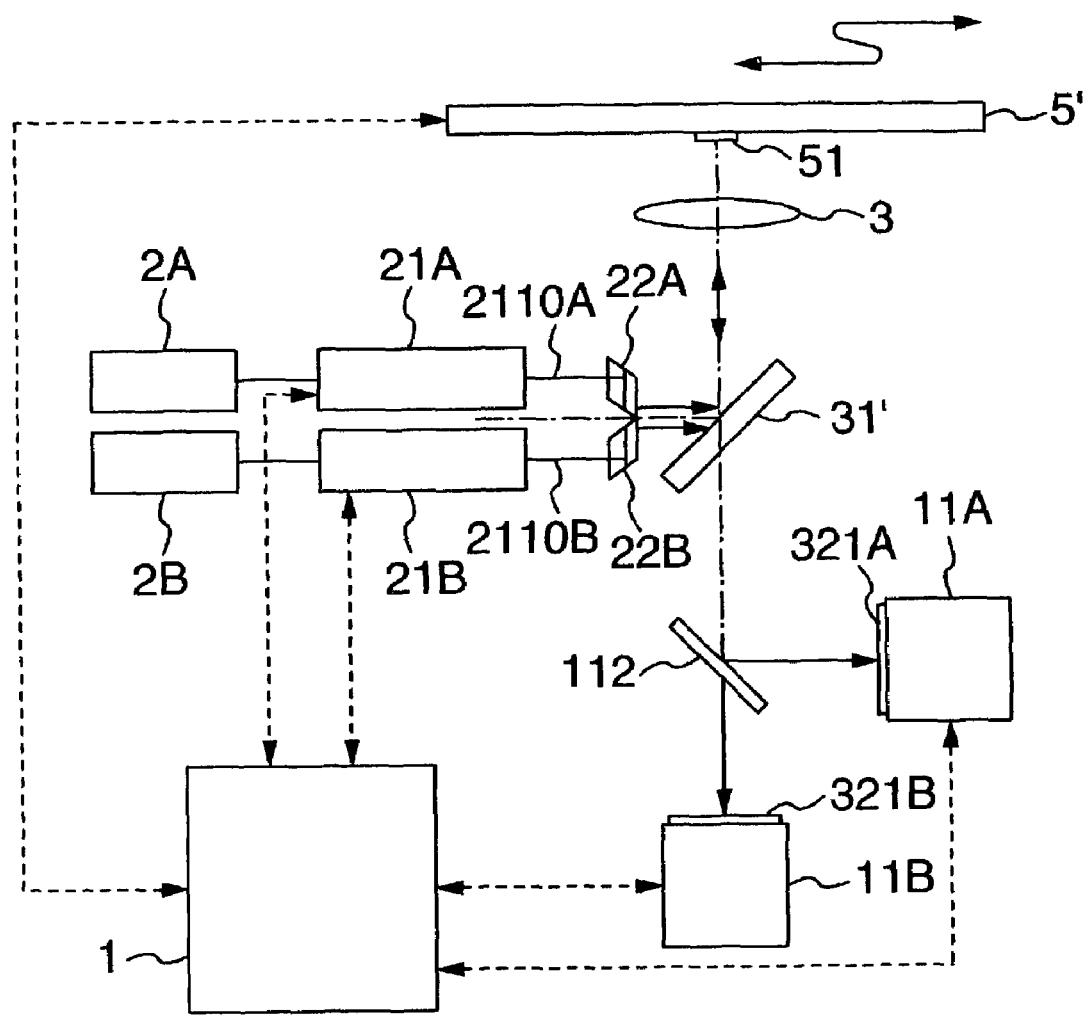
FIG. 6 is a front view illustrating a schematic structure of a third working example of an apparatus for inspecting a DNA according to the present invention.

FIG. 6 is a schematic diagram illustrating a third working example of the present invention, wherein a DNA is inspected in a wide dynamic range, at high speed and with high sensitivity. Each of the reference numerals "2A" and "2B" represents an excitation laser light source which generates a laser light having a wavelength different from each other, which can excite the objective of inspection of a DNA in a sample (5'). The numerals "2A" and "2B" generate a laser light with a wavelength of 488 nm and a laser light with a wavelength of 532 nm, respectively. The output of each of the laser lights is in the range of 100 to 200 mW. The sample (5') is in the form of what is called a DNA micro-array, which is a sample wherein a target DNA to which a fluorescence label is added is hybridized to a probe DNA on a substrate (5'). Each of the laser lights emitted from the two types of excitation laser light sources (2A and 2B) forms a multibeam as shown in FIG. 10 hereinafter.

Figure 10:
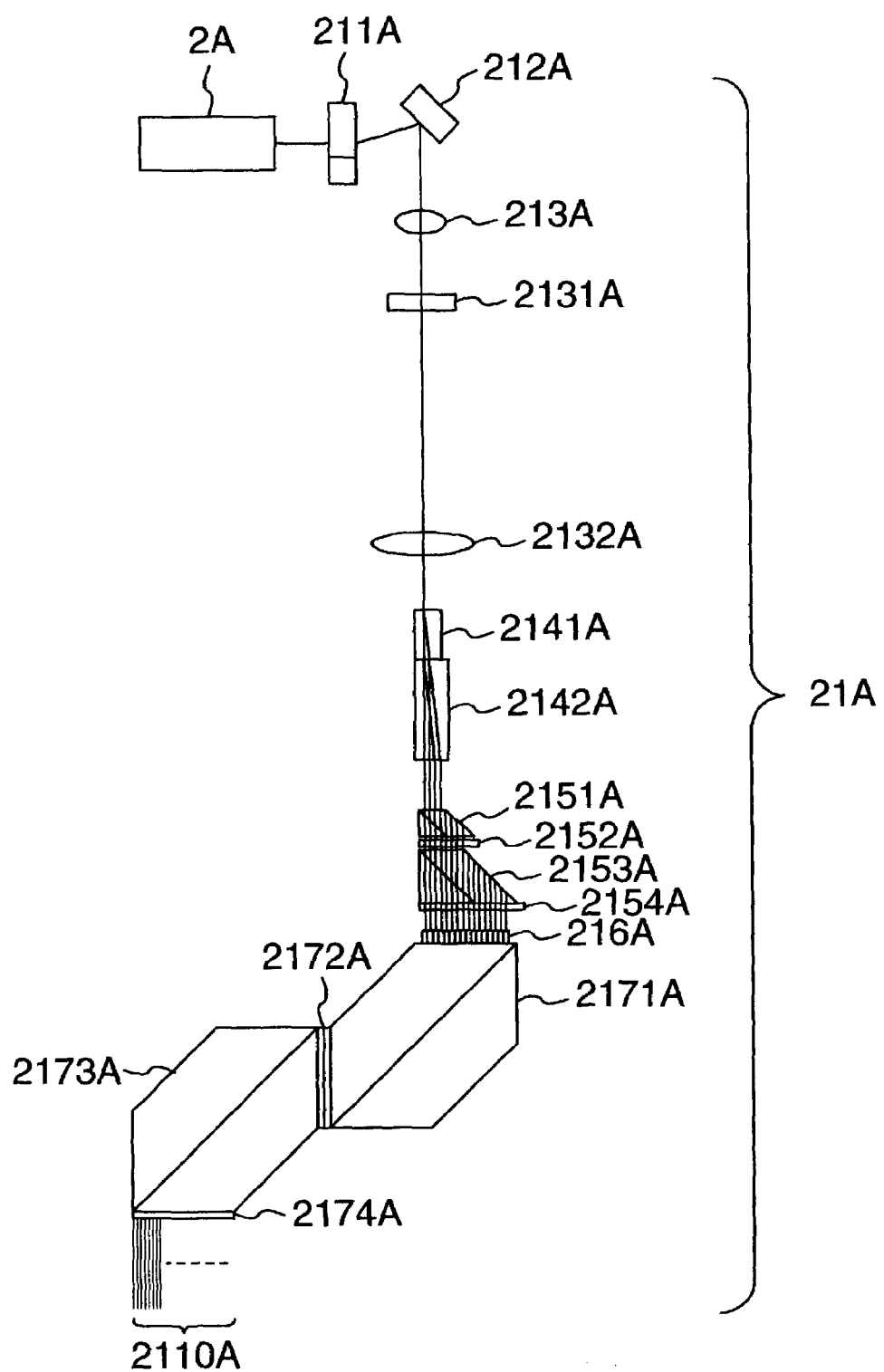
FIG. 10 is a front view illustrating the basic constitution of an optical system for obtaining a multispot light from an excitation laser light source in the present invention.

FIG. 10 illustrates an exciting light system having a wavelength of 488 nm, while an exciting light system having a wavelength of 532 nm is also constituted in the same manner. In FIG. 10, the intensity of the laser light emitted from the light source (2A) can be changed on the basis of a signal from a control circuit (1) by means of a well-known AO-modulator (211A) at a switching rate of microseconds. An exciting light as obtained as a primary diffracted light is passed through a mirror (212A), a first collimator lens (213A), a pinhole mask (2131A) and a second collimator lens (2132A) so as to form a desired diameter and angle of divergence of the beam, and thereafter comes into multibeam generators as explained hereinafter.

Each of the numerals (2141A and 2142A) represents the multibeam generator comprising a calcite element, wherein when one beam comes into the multibeam generator (2141A), the beam outgoes as branched four beams from the multibeam generator (2142A). Incidentally, quarter-wave plates (not shown) are incorporated between both calcite elements and on the emitting surface of the multibeam generator (2142A). After the outgoing radiation of the four beams from the multibeam generator (2142A), these four beams are formed into alternate right-handed circularly polarized light and left-handed circularly polarized light. These four beams then come into a pair of prisms (2151A and 2153A) each of which comprises a parallelogrammatic body and an isosceles right triangled body, which are bonded to each other, wherein the bonded surface acts as a polarization beam splitter. The ratio of the first polarizing prism (2151A) to the second polarizing prism (2153A) in dimension is of 1:2. The quarter-wave plates (2152A and 5154A) are incorporated between the first and second polarizing prisms (2151A and 2153A), and on the emitting surface of the second polarizing prism (2153A), respectively. The four incident beams are branched into sixteen beams through these two prisms.

Each of the sixteen beams is narrowed down into a spot-light having a diameter of 40 μm by means of a microlenses array (216A), and then comes into a first pair of trapezoidal prisms (2171A) which comprises first and second trapezoidal prisms, wherein the first trapezoidal prism is slightly different in thickness (or height) from the second trapezoidal prism, and the wider bottom face of the first trapezoidal prism is bonded to that of the second trapezoidal prism. The above sixteen beams are branched into thirty-two beams through the first pair of trapezoidal prisms (2171A), each of the sixteen beams being branched into two beams with a half pitch. A quarter-wave plate (2172A) is incorporated on the emitting surface of the first pair of trapezoidal prisms (2171A), whereby the thirty-two beams are formed into alternate right-handed circularly polarized light and left-handed circularly polarized light.

The thirty-two beams through the first pair of trapezoidal prisms (2171A) come into a second pair of trapezoidal prisms (2173A) which comprises third and fourth trapezoidal prisms, and has a structure similar to that of the first pair of trapezoidal prisms (2171A) explained above, wherein the difference in thickness between the third and fourth trapezoidal prisms is half of the one between the first and second trapezoidal prisms. Then each of the thirty-two beams is branched into two beams with a half pitch, and thus the thirty-two beams are emitted in the form of sixty-four beams. The sixty-four beams are then passed through a quarter-wave plate (2174A) as incorporated on the emitting surface of the second pair of trapezoidal prisms (2173A), whereby the sixty-four beams (2110A) in the form of alternate right-handed circularly polarized light and left-handed circularly polarized light can be obtained.

The sixty-four multibeam (2110A), which has started from the light source (2A) and has been provided through the multispot optical system (21A), and the other sixty-four multibeam (2110B) which has started from the light source (2B) which generates a laser light having a wavelength of 532 nm, and has been provided through the multispot optical system (21B) which is the same optical system as the multispot optical system (21A) come into regulators (22A and 22B) for controlling a space between beams, respectively. The multibeams with two colors which have been passed through the regulators (22A and 22B) are reflected from a wavelengths-selecting beam splitter (31'), and passed through an object lens (3) with a large NA, with which fluorescence labels in the samples (5') can be irradiated and excited in state of multispot lights.

Figure 7:
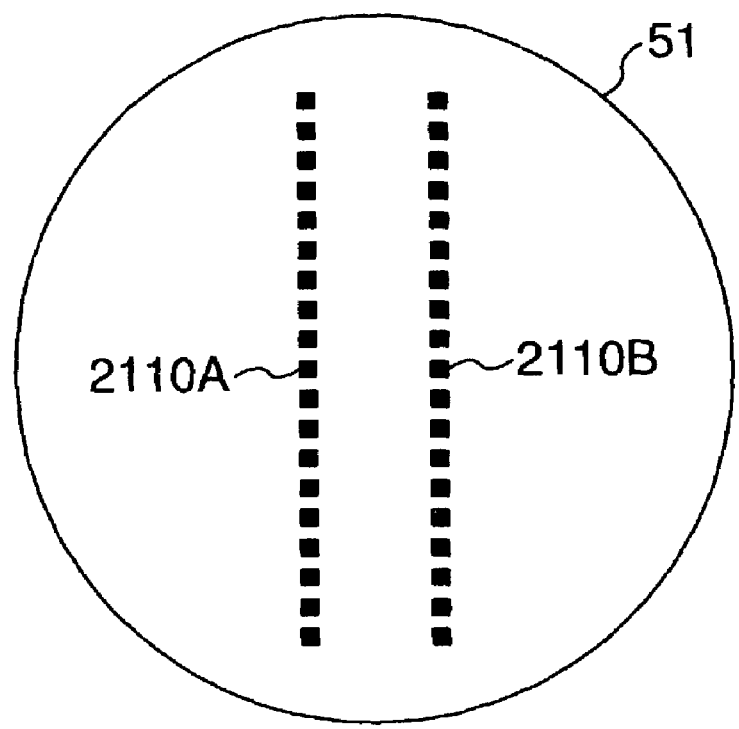
FIG. 7 is a plan view in the visual field of an object lens, demonstrating a multispot array of exciting lights with two color as irradiated on samples in the present invention.

FIG. 7 demonstrates the state of the multispot lights of two colors irradiating the top of the samples (5'), wherein the reference numeral "51" represents the visual field of the object lens (3); the numeral "2110A" represents a multispot exciting-lights consisting of the sixty-four spot-lights having a wavelength of 488 nm; and the numeral "2110B" represents a multispot exciting-lights consisting of the sixty-four spot lights having a wavelength of 532 nm. The samples (5') are scanned in a direction indicated by the arrow shown in FIG. 5, namely in a direction orthogonal to the array direction of the sixty-four multispot array shown in FIG. 7.

The spot diameter of one of the multispot lights is decided on the basis of resolution required for the sample. In this working example, the spot diameter is 2 μm, and the pitch between the spots is 20 μm.

As shown in FIG. 6, fluorescent lights which have been generated by excitation with the two exciting lights as mentioned above are passed through the object lens (3) and the wavelengths-selecting beam splitter (31'), and then branched into two fluorescent lights with a fluorescence waveband different from each other by means of a fluorescent-lights separating mirror (112) so that the samples can be separately detected with each of the two fluorescence wavelengths. That is to say, a fluorescent light having a wavelength of approximately 500 nm as generated with an exciting light having a wavelength of 488 nm is reflected from the fluorescent-lights separating mirror (112), and is transmitted through an influence filter (321A) having the center of wave ranges at a wavelength of 500 nm, and then comes into a sixty-four channel photo-multiplier (11A). On the other hand, a fluorescent light having a wavelength of approximately 570 nm as generated with an exciting light having a wavelength of 532 nm is transmitted through the fluorescent-lights separating mirror (112), and is transmitted through an influence filter (321B) having the center of wave ranges at a wavelength of 570 nm, and then comes into a sixty-four channel photo-multiplier (11B).

Figure 8:
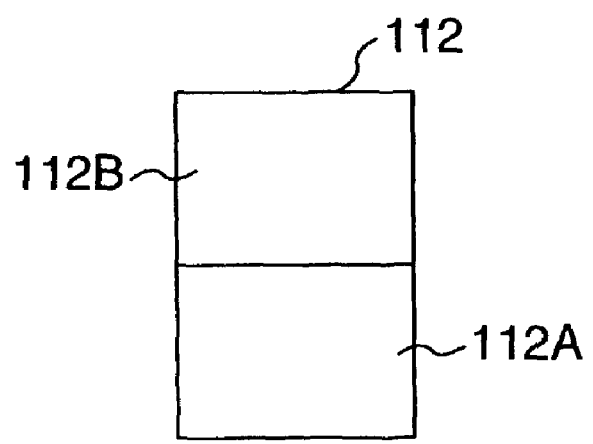
FIG. 8 is a front view of a fluorescent-lights separating mirror for separating two types of fluorescent lights in the present invention.
Figure 9:
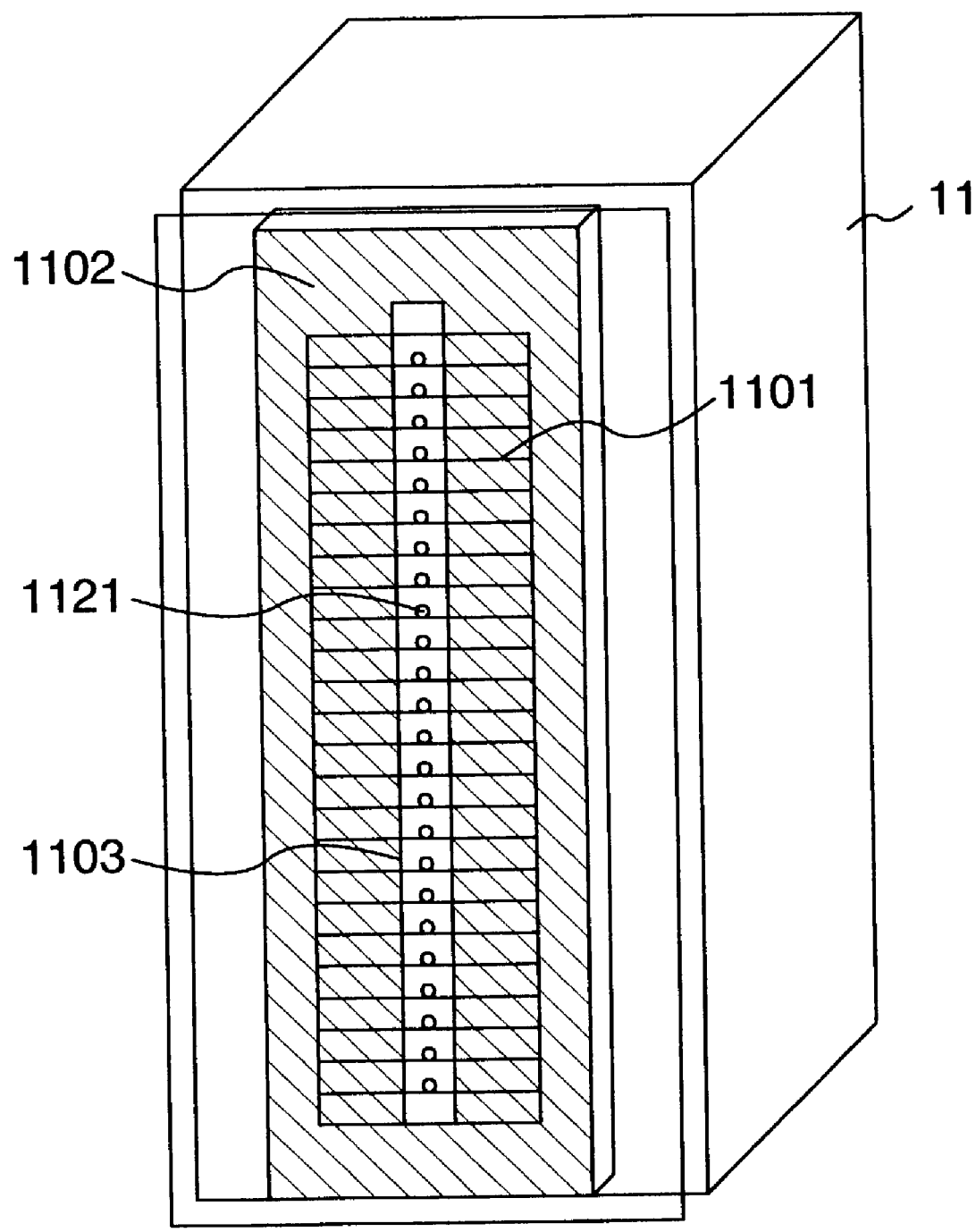
FIG. 9 is a perspective diagram of a multichannel photo-multiplier for detecting fluorescent lights as emitted with multispot lights in the present invention.

As shown in FIG. 8, the lower half (112A) of the fluorescent-lights separating mirror (112) reflects a wavelength of 500 nm and transmits a wavelength of 570 nm, while the upper half (112B) thereof transmits a wavelength of 500 nm and reflects a wavelength of 570 nm. FIG. 9 is a detailed drawing of the photo-multiplier (11A or 11B), wherein the photo-multiplier (11A and 11B) are expediently represented by a photo-multiplier (11) in explanation. In FIG. 9, a mask (1102) is disposed in the front of photo-multiplier (11); the mask (1102) is disposed in front of an aperture array (1101) with sixty-four channels; and a narrow slit (1103) is formed in the center section of the photo-multiplier (11). A fluorescent light corresponding to each of multispot lights, which has been generated by exciting the samples (5') with the multispot lights, is imaged as a fluorescent spot image (1121) on each of the apertures of the multichannel photo-multiplier (11) through the object lens (3).

In this way, a fluorescent light from each of spots upon the samples (5') is separately detected; that is, the signal of photon pulses count is simultaneously obtained as sixty-four data corresponding to each of the exciting laser lights by means of the control circuit (1) as shown in FIG. 6. The samples (5') are scanned in a direction orthogonal to the multispot array as mentioned above. When the scanning has been scanned to the end of the samples (5'), the stage is shifted by the diameter of a spot in a direction of the row of the multispot array, and then the samples (5') are scanned in the direction opposite to the above direction orthogonal to the multispot array. Thus such scanning is repeated so as to detect fluorescent lights, whereby fluorescent lights in a desired area of the samples (5') can be detected.

On this occasion, if the time "T" that an exciting light passes by one picture element is divided into two section, and the intensity of an exciting light is varied by means of the AO-modulators (211A and/or 211B) as stated previously so as to detect fluorescent lights, detection in a wide dynamic range can be achieved.

Hereinafter, a working example wherein the detection of fluorescence is carried out with an exciting light having two or three phases in intensity so as to will be explained. In this working example, a detection time "T" in each of the phases of the intensity of an exciting light is taken as 40 μs, a photon pulse width "ΔT" is taken as 10 ns, and this pulse width "ΔT" is divided into m (for example, m=1000) equal divisions. Hereafter let "ΔT/m" be a sampling point of time. Furthermore, let the number of photon pulses as detected in the detection time "T" be n. Observing any one point of time in the detection time "T", let the signal of a photon pulse rise at this observation point of time "$t_o$,". When T/ΔT is represented by N, the probability "p" that the signal of a photon pulse will rise at each of sampling points is n/Nm, and thus the probability that the signal of a photon pulse will not rise at (m+1) of sampling points before the observation point of time mentioned above is $(1-p)^{m+1}$. That is to say, the probability "$p_o$" that an observed photon pulse is not superposed upon the following pulse is given by the following formula (1):

$$p_o = (1-p)^{m+1} \quad (1)$$

wherein $p = n/Nm$ (2)

Conversely, the probability that the observed photon pulse is followed by another pulse, and the observed photon pulse is superposed upon the following pulse is given by $(1-p_o)$. Therefore, the probability that the two photon pulses are continuously arrayed is $p_o(1-p_o)$. This is because the following photon pulse above rises with a probability of $(1-p_o)$ during the time "ΔT" following the observed photon pulse, and the following photon pulse above does not rise with a probability of $p_o$ during the time "ΔT" following the observed photon pulse. In the same way, the probability that m of photon pulses are superposed upon one another is $p_o(1-p_o)^m$.

Consequently, if no photon pulses are superposed in the detection time "T", photon pulses are counted "n" times on the average in the detection time "T". Actually, however, some photon pulses are superposed therein, and thus the number of photon pulses count is decreased. The number "$d_n$" of photon pulses count as decreased is represented by the following formula (3):

$$d_n = n \sum_{m=1}^{\infty} (m-1) p_o (1-p_o)^m$$

$$= n \frac{(1-p_o)^2}{p_o}$$

Accordingly, the number "$n_e$" of photon pulses count as detected in the detection time "T" is represented by the following formula (4):

$$n_e = n - d_n$$

$$= n \left( 1 - \frac{(1-p_o)^2}{p_o} \right)$$

This formula (4) approximately represents a curve as shown in FIG. 4.

In FIG. 4, the time "T" as required for detecting one picture element is 40 μs, and the time width "ΔT" of the signal of a photon pulse is 10 ns. Accordingly, the value of "N" mentioned above is N=T/ΔT=4000. When letting m=1000, the formulae (1) to (4) mentioned above are used, the number "$n_e$" of photon pulses count as actually detected to the average number "n" of photon pulses in the detection time "T" is shown in Table 1.

TABLE 1

| No. of Photon Pulses (n) | No. of Photon Pulses Count ($n_e$) |
|---|---|
| 200 | 199.6 |
| 400 | 396.0 |
| 600 | 586.5 |
| 800 | 767.8 |
| 1000 | 937.0 |
| 1200 | 1090.9 |
| 1400 | 1226.3 |
| 1600 | 1339.9 |
| 1800 | 1428.4 |
| 2000 | 1488.2 |
| 2200 | 1515.7 |
| 2400 | 1507.4 |
| 2600 | 1459.2 |
| 2800 | 1367.0 |
| 3000 | 1226.8 |
| 3200 | 1033.6 |
| 3400 | 784.1 |
| 3600 | 472.1 |
| 3800 | 92.9 |

As can be taken from FIG. 4 or Table 1, when the average number "n" of photon pulses is approximately 2200, the number "$n_e$" of photon pulses count reaches a maximum at approximately 1515, and when the number "n" is further increased, the number "$n_e$" is decreased. Furthermore, the differential coefficient of the curve in FIG. 4 is decreased near the maximum value of the number "$n_e$" of photon pulses count, which results in a decreased accuracy of an estimation of photon pulses. Therefore, in this working example, values up to approximately 1400 will be used as the number "$n_e$" of photon pulses count.

When the number "$n_e$" of photon pulses count is 1400 or less, there are two candidate values for the number "n" of photon pulses. In such a case, the lower candidate value shall be employed. Furthermore, since the relationship between the number "n" and the number "$n_e$" is not linear, such a relation whose outline is shown in Table 1 shall be prepared as a numeric table, whereby the true number "n" of photon pulses can be calculated from the number "$n_e$" of photon pulses count as detected. Without using the numeric table mentioned above, the relationship between the number "n" and the number "$n_e$" may be approximated by an approximate formula, that is to say, the number "n" may be approximated by the function expression "$n(n_e)$" of $n_e$, so as to determine the number "n" from the number "$n_e$".

Thus, when the number "n" of photon pulses is increased, the number "$n_e$" of photon pulses count is decreased. Accordingly, as specifically explained hereinafter, an exciting light is changed into two or three phases in intensity so as to detect fluorescence. Tables 2 and 3 demonstrate a working example wherein fluorescence is detected with an exciting light changed into two and three phases in intensity, respectively, wherein as the detection time "T" and the time width "ΔT" of photon pulses, let the above-mentioned ones used for explaining Table 1 be used.

TABLE 2

| No. of Photon Pulses (n) | No. of Photon Pulses Count with Strong Exciting Light ($I_s$) ($n_{es}$) | No. of Photon Pulses Count with Weak Exciting Light ($I_w$) ($n_{ew}$) |
|---|---|---|
| 20000 | (0) | 937 |
| 10000 | (0) | 396 |
| 4000 | (0) | 200 |
| 2000 | 1488 | 100 |
| 1000 | 937 | 50 |
| 400 | 396 | 20 |
| 200 | 200 | 10 |
| 100 | 100 | 5 |
| 40 | 40 | 2 |
| 20 | 20 | 1 |
| 10 | 10 | 0 |
| 4 | 4 | 0 |
| 2 | 2 | 0 |
| 1 | 1 | 0 |

Table 2 demonstrates a case wherein a fluorescent material is excited with a fluorescent light having the two phases "$I_s$" and "$I_w$" in intensity, wherein the intensity of the phase "$I_w$" is one twentieth of that of the phase "$I_s$". When the number ($n_{es}$) of photon pulses count with an exciting light having the intensity "$I_s$" is from 1 to 1200, and the number ($n_{ew}$) of photon pulses count with an exciting light having the intensity "$I_w$" is 60 or less, the number ($n_{es}$) with an exciting light having the intensity "$I_s$" which is enclosed by the thick frame of the central column (i.e., the column of $n_{es}$) in Table 2 shall be employed, while the number ($n_{ew}$) of photon pulses count with an exciting light having the intensity "$I_w$" is 60 or more, the number ($n_{ew}$) with an exciting light having the intensity "$I_w$" which is enclosed by the thick frame of the column (i.e., the column of $n_{ew}$) of the right edge in Table 2 shall be employed, whereby photon pulses in the range of 1 to 20000 can be detected by taking the time "T" of 80 µs as required for detecting one picture element, which means that according to the present invention the dynamic range has been remarkably improved, considering that a conventional limitation of detecting fluorescence with an exciting light with a certain fixed level in intensity was approximately 1 to 3000.

According to the above explanation, the minimum level of the number ($n_{es}$) of photon pulses count is explained to be 1. However, since the detection of photon pulses is carried out at random, even when the number ($n_{nes}$) of photon pulses count is 1, it may be counted as zero. Therefore, letting the minimum level of the number of photon pulses count be 4, the limit of a dynamic range according to the present invention is 5000, while the one according to the prior art is 750.

TABLE 3

| No. of Photon Pulses (n) | No. of Photon Pulses Count with Strong Exciting Light ($I_s$) ($n_{es}$) | No. of Photon Pulses Count with Middle Exciting Light ($I_m$) ($n_{em}$) | No. of Photon Pulses Count with Weak Exciting Light ($I_w$) ($n_{ew}$) |
|---|---|---|---|
| 200000 | (0) | (0) | 1488 |
| 100000 | (0) | (0) | 937 |
| 40000 | (0) | (0) | 396 |
| 20000 | (0) | 1488 | 200 |
| 10000 | (0) | 937 | 100 |
| 4000 | (0) | 396 | 40 |
| 2000 | 1488 | 200 | 20 |
| 1000 | 937 | 100 | 10 |
| 400 | 396 | 40 | 4 |
| 200 | 200 | 20 | 2 |
| 100 | 100 | 10 | 1 |
| 40 | 40 | 4 | 0 |
| 20 | 20 | 2 | 0 |
| 10 | 10 | 1 | 0 |
| 4 | 4 | 0 | 0 |
| 2 | 2 | 0 | 0 |
| 1 | 1 | 0 | 0 |

Table 3 demonstrates a case wherein a fluorescent material is excited with an exciting light having the three phases "$I_s$", "$I_m$" and "$I_w$" in intensity, wherein the ratio of $I_s:I_m:I_w$ is 100:10:1.

When the number ($n_{es}$) of photon pulses count with an exciting light having the intensity "$I_s$" is from 1 to 1200, and the number ($n_{em}$) of photon pulses count with an exciting light having the intensity "$I_m$" is 120 or less, the number ($n_{es}$) with an exciting light having the intensity "$I_s$" which is enclosed by the thick frame of the second column (i.e., the column of $n_{es}$) from the left in Table 3 shall be employed, while the number ($n_{es}$) of photon pulses count with an exciting light having the intensity "$I_m$" is from 120 to 1200, and the number ($n_{ew}$) of photon pulses count with an exciting light having the intensity "$I_w$" is 120 or less, the number ($n_{em}$) with an exciting light having the intensity "$I_m$" which is enclosed by the thick frame of the second column (i.e., the column of $n_{em}$) from the right in Table 3 shall be employed, while the number ($n_{ew}$) of photon pulses count with an exciting light having the intensity "$I_w$" is 120 or more, the number ($n_{ew}$) with an exciting light having the intensity "$I_w$" which is enclosed by the thick frame of the column (i.e., the column of $n_{ew}$) of the right edge in Table 3 shall be employed, whereby photon pulses in the range of 1 to 200000 can be detected.

In the same manner as the one explained on Table 2, letting the minimum level of the number of photon pulses be 4, the limit of a dynamic range according to the present invention is 50000, whereby the detection of fluorescence can be carried out in an extraordinarily wide dynamic range as compared with the prior art. Incidentally, letting the aforementioned minimum level of the number of photon pulses be 16, the limit of a dynamic range according to the present invention is 12500.

An improvement in the dynamic range as explained with reference to Table 2 or 3 gives rise to the detection of fluorescence with an exciting light changed into two or three phases in intensity. However, even when an exciting light for detecting fluorescence as explained with reference to FIG. 5 is branched into two or three beams at a ratio of 1:20 or 1:10:100 so as to detect the resultant two or three beams of fluorescence by means of two or three photo-multipliers, a similar result to the one mentioned above can be obtained. In this case, since the detection of fluorescence is carried out in parallel, the detection time is decreased to half of the one for detection with an exciting light having two phases in intensity, or one third of the one for detection with exciting lights having three phases in intensity.

In the working example mentioned above, the only value of fluorescence as generated with an exciting light having any one proper phase in intensity is employed as a final value. However, a weighted average from two data near an area wherein a data to be employed is switched from a column in Table 2 or 3 to another column can be calculated so as to provide as a final data. For example, within the boundary between 1000 and 2000 of the number (n) of photon pulses in Table 2, the number (n on $n_{es}$) of photon pulses as determined by using the column of the number ($n_{es}$) of photon pulses count in Table 2, said number ($n_{es}$) being obtained with an exciting light having the intensity ($I_s$), and the number (n on $n_{ew}$) of photon pulses as determined by using the column of the number ($n_{ew}$) of photon pulses count in Table 2, said number ($n_{ew}$) being obtained with an exciting light having the intensity ($I_w$) are employed.

The number ($n_o$) of photon pulses from both the number (n on $n_{es}$) and the number (n on $n_{ew}$) is calculated by using the following formula (5):

$$n_o = [\alpha \times 20 \times (n \text{ on } n_{es}) + \beta \times (n \text{ on } n_{ew})]/(\alpha+\beta) \quad (5)$$

wherein "20" is the ratio of the intensity ($I_s$) to the intensity ($I_w$); $\alpha$ represents a weighted coefficient for the number (n on $n_{es}$); and $\beta$ represents a weighted coefficient for the number (n on $n_{ew}$), wherein for example, the weighted coefficients having the following formulae:

$$\alpha = [1500-(n_{es})] \times (n_{es})/100000$$

$$\beta = (n_{ew})^2/1000 \quad (6)$$

shall be employed.

In this manner, when the intensity ($I_s$) is about 1200 or more, the intensity ($I_w$) of an exciting light is exponentially weighted. Conversely, when the intensity ($I_s$) is about 1200 or less, the intensity ($I_s$) of an exciting light is exponentially weighted.

Consequently, a value in portions as enclosed by the thick frames of the columns in Table 2 is automatically and primarily employed. Other various methods of weighting the numbers ($n_{es}$ and $n_{ew}$) of photon pulses count as well as the method mentioned above can be proposed wherein it is preferred that the relationship between the number (n) of photon pulses and the numbers ($n_{es}$ and $n_{ew}$) of photon pulses count is carefully examined and determined.

Information on the number ($n_o$) of photon pulses as determined in such a manner as explained above shall be memorized in a memory means, together with information on the position of a probe DNA in a sample. Then, preferably, inspection conditions, information on the probe DNA, information on the sample and the like also shall be memorized all together by relating to information mentioned above.

Information as memorized in such a manner may be compared with further information which was separately memorized so that the state of a DNA as detected with fluorescence can be inspected and/or estimated.

Furthermore, information on the number ($n_o$) of photon pulses as determined above may be displayed on a display (not shown), together with information on the position of a probe DNA in a sample so that the result can be submitted for an operator's perusal.

Besides, information on the number ($n_o$) of photon pulses as determined above may be transmitted to an analysis system and/or an inspection system or the like for use.

Although an exciting light having two phases in intensity is used in the working example mentioned above, an exciting light having three or more phases in intensity also may be used. Furthermore, the reference numeral "5'" has been described as a DNA micro-array, it may be any object provided that the object includes a material having fluorescent properties. Thus the present invention can be applied to the detection of proteins as well. Incidentally, it is not necessary that the object of detection be what is fixed on a substrate. The object of detection may be samples in the form of one- or two-dimensional array of bead, or liquids or solids including a fluorescent material in capillary tubes.

Hereinbefore, the detection of fluorescence mentioned above has been explained with reference to merely the working examples wherein two-dimensional images are obtained by scanning. However, it is obvious that the present invention can be realized by detecting fluorescence as generated with an exciting light having two or more strong and weak phases in intensity by means of a two-dimensional imaging device as well.

As explained above, according to the present invention, even samples wherein the density of a fluorescent molecule is different according to a detected site by a thousand times or more, or ten-thousands times or more can be quantitatively detected in a wide dynamic range, and further can be detected at high sensitivity with the wide dynamic range maintained.

In addition, according to the present invention, in order to detect fluorescence in such a dynamic range with high sensitivity, multispot beams can be employed, whereby the time required to detect a fluorescent light as emitted from the whole area of a sample can be remarkably decreased, whereby a high-throughput and high-speed detection of fluorescence can be achieved.

As a result, the present invention will provide advantageous effects in fields, in particular, such as a field of analysis of DNA-expression in the future wherein a wide-dynamic range, high-sensitivity and high-speed detection of fluorescence is required.

Next, a method of inspecting samples, wherein a technology for detecting a DNA in a wide dynamic range at high speed with high sensitivity according to the present invention as explained above is applied to the detection of fluorescence as emitted from the samples wherein beads or dots are arrayed in the form of an array, and an apparatus for carrying out the same will be explained hereinafter.

Figure 11:
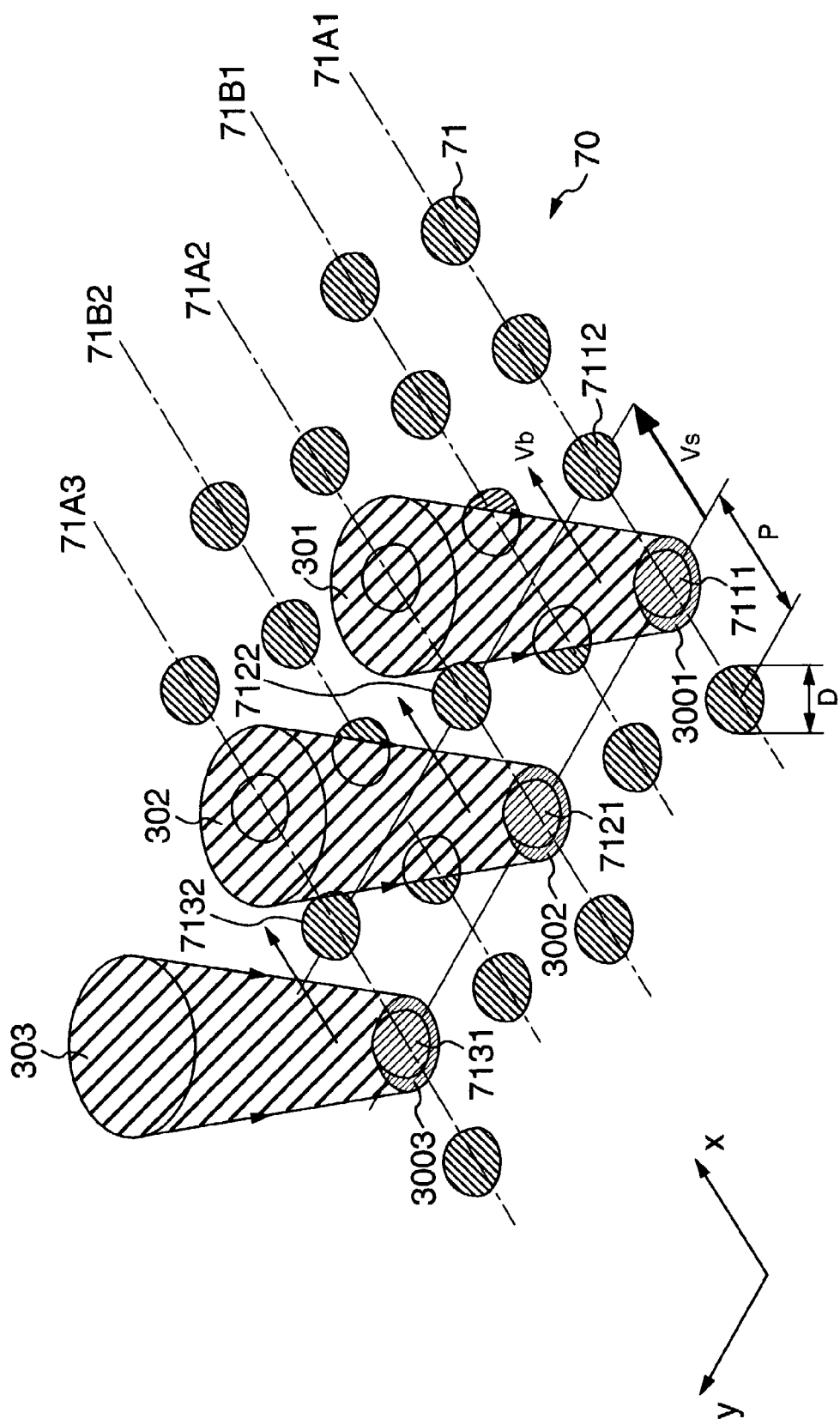
FIG. 11 is a perspective diagram of samples in the form of a bead-array, illustrating a state wherein fluorescence on the arrayed beads is detected according to the present invention.

FIG. 11 shows a state wherein a lot of beads (71) are arrayed in the form of a honeycomb structure with closest-packing on a two-dimensional plane of the surface of a substrate, provided that P>D wherein "P" represents a pitch between each of the beads (71) and an adjacent bead, and "D" represents the diameter of each of the beads (71)], and a fluorescence-labeled DNA of each of DNA samples (70) is attached to the surface of each of the beads (71), so that the DNA samples (70) can be arrayed in the form of a bead-array; the DNA samples (70) are irradiated with the beams (301, 302, 303, . . . ) of exciting light for the detection of fluorescence wherein the centers (3001, 3002, 3003, . . . ) of the beads (7111, 7121, 7131, . . . ) are irradiated with the beams (301, 302, 303, . . . ) of exciting light so as to irradiate the upper sides of the DNA samples (70), wherein the DNA samples (70) in the form of a bead-array are continuously scanned at a uniform speed ($V_s$) in an x-direction as indicated by a thick arrow by means of an x-stage (not shown).

Figure 12A:
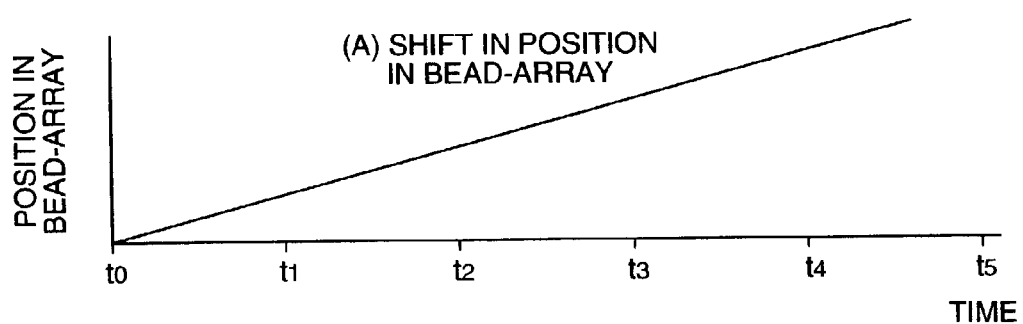
FIG. 12A is a graph illustrating a shift in the position of the bead-array in the present invention.
Figure 12B:
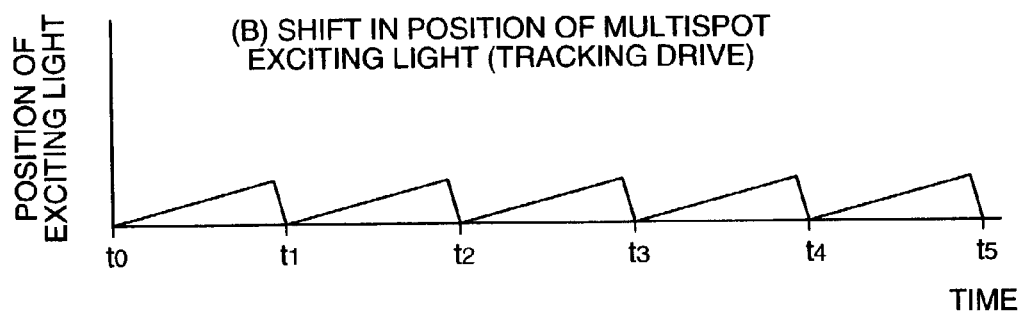
FIG. 12B is a graph illustrating a shift in the position of multispot exciting lights in the present invention.

Accordingly, as shown in FIG. 12A, letting the time when the centers (3001, 3002, 3003, . . . ) of the beads (7111, 7121, 7131, . . . ) are irradiated with the beams (301, 302, 303, . . . ) of exciting light respectively as shown in FIG. 11 be the time "$t_1$", at the time "$t_2$" after the lapsed time $\Delta t$ ($=t_{n++1}-t_n$), the centers of the beads (7112, 7122, 7132, . . . ) as shown in FIG. 11 will be irradiated with the beams (301, 302, 303, . . . ) respectively, the centers of the beads (7112, 7122, 7132, . . . ) being separated from those of the beads (7111, 7121, 7131, . . . ) respectively by an array pitch "P" of the beads. That is to say, in FIG. 11, the beams (301, 302, 303, . . . ) of exciting light travel at a speed of $V_b$ in an x-direction as shown by a thick arrow, with approximately $V_b \approx V_s$ wherein $V_b$ represents a travelling speed of the beams (301, 302, 303, . . . ), and $V_s$ represents a travelling speed of the x-stage. When the beams (301, 302, 303, . . . ) have traveled near to the beads (7112, 7122, 7132, . . . ) respectively, the position of the beams is brought back to the initial position (301, 302, 303, . . . ) as shown in FIG. 12B, and then at the time "$t_2$", the beams (301, 302, 303, . . . ) again travel at a speed of $V_b$ in an x-direction.

This operation is repeated every time the beams of exciting light have traveled by the array pitch "P" of the beads. When the beams of exciting light have attained the last beads as arrayed in an x-direction, the DNA samples (70) are moved by $\sqrt{3}P/2$ in a minus (−) y-direction by means of a y-stage (not shown), whereby the lines (71B1, 71B2, 71B3, . . . ) which lie next to the lines (71A1, 71A2, 71A3, . . . ) as shown in FIG. 11, which have been detected till now, can be detected according to the manner as mentioned above. When the detection of the lines (71B1, 71B2, 71B3, . . . ) have been finished, the DNA samples (70) are moved in a minus (−) y-direction by $\sqrt{3}P(N-\frac{1}{2})$ wherein "N" represents the number of spots of the multispot, and thus the operation for detection mentioned above is repeated, whereby the beads over the whole surface can be detected.

As can be easily taken from the above explanation, the time required for scanning by one pitch in the bead-array is almost taken over for irradiating the beads with the exciting lights, and thus the detection of fluorescence can be carried out within this time. On the other hand, when the whole surface of samples is scanned with merely a stage traveling without beams of exciting light traveling in the prior art, letting the scanning speed "$V_s$" is the same as a travelling speed of the x-stage in the present invention, a time for detection is only $D/V_s$, which is a time required for passing each of the beams through each of beads by the diameter of bead, while according to a method of the present invention, a time during $P/V_s$ can be used for detection. Furthermore, when the whole surface of each of samples is scanned in the prior art, a space between each of beads and an adjacent bead is also scanned, and thus the number of times for step-moving beams in a y-direction is increased by $\sqrt{3}P/2D$ times as compared to the one in the present invention, and thus a time required for detecting all the samples is increased.

Thus the employment of a method of the present invention increases a time required for detecting one bead, whereby even when a fluorescent light is weak and the intensity of the fluorescent light is detected according to a photon counting method, more photons can enter a detector, and thus a high-sensitive detection can be achieved. Furthermore, a time for detecting the whole surface of each of samples is decreased, whereby the high-speed detection of fluorescence can be achieved.

Incidentally, in this case, as explained with reference to FIGS. 2A and 2B, the intensity of an exciting light is switched within the period of time when one bead is irradiated with the exciting light so that a fluorescent light can be detected corresponding to each of the exciting lights with the intensity switched, whereby samples can be detected with high sensitivity in a wider dynamic-range.

Figure 13:
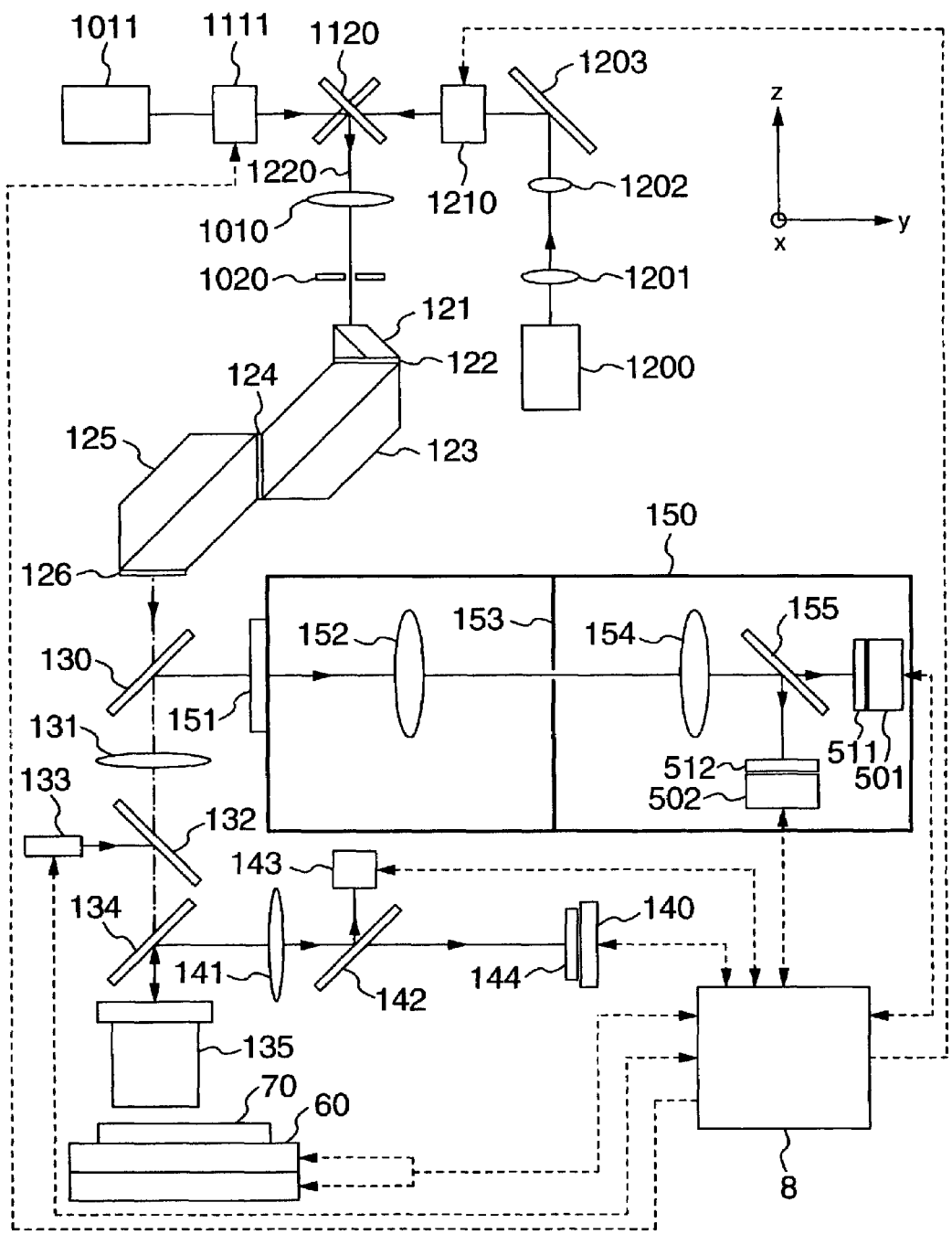
FIG. 13 is a front view illustrating the schematic constitution of a fluorescence bead-array detector according to the present invention.

FIG. 13 is a schematic diagram illustrating the structure of an apparatus for detecting fluorescence on beads or an apparatus for inspecting DNAs with fluorescence on beads, wherein the reference numeral "1011" represents an exciting laser light source for generating a laser light with a wavelength of 488 nm, and the reference numeral "1200" represents a laser light source for generating a laser light with a wavelength of 532 nm. According to need, each laser beam is formed into the desired diameter of a laser beam through a beam forming optical system (1201 or 1202) as shown in FIG. 13. Each laser beam as formed into the desired diameter comes into an AO-modulator (or an acoustic-optic deflector & amp. modulator)(1111 or 1210).

Each of the AO-modulators (1111 and 1210) can change the angle of diffraction of an outgoing laser beam by changing the frequency of a high-frequency signal coming into an ultrasonic transducer of a quartz crystal which is mounted in each of the AO-modulators (1111 and 1210), and furthermore can change the intensity of the outgoing laser beam by changing the amplitude of the input high-frequency signal.

The optical axis of each of the laser beams slightly deviates in a direction perpendicular to the plane surface of FIG. 13, and thus each of the laser beam with a wavelength of 488 nm and the laser beam with a wavelength of 532 nm goes ahead in a minus (−) z-direction (downward) with a slight displacement as well as with an angle slightly deviated from a parallel. Each of the two laser beams comes into a convex lens (1010), and goes on its way in parallel to the other beam, and thereafter comes into a pinhole plate (1020) with two pinholes. After each of the two laser beams has been passed through each of the two pinholes, it is passed through a first polarized-beam splitter (121), whereby each of the two laser beams is branched into two beams having a spacing "W". The two beams having each wavelength are linearly polarized lights which are orthogonal to each other, and are passed through a quarter-wave plate (122) so as to form right- and left-handed circularly polarized lights, and thereafter come into a first pair of bonded trapezoidal prisms (123). The bonding portion of the first pair of bonded trapezoidal prisms (123) comprising first and second trapezoidal prisms forms a polarized-beam splitter. Since two trapezoidal prisms are slightly different in height from each other, when the laser beams having each wavelength come into a quarter-wave plate (124), the laser beams having each wavelength are formed into four beams which have a spacing "(½)W", and are linearly polarized lights which are alternately orthogonal.

When the four beams having each wavelength have been passed through the quarter-wave plate (124), the four beams are formed into alternate right-handed circularly polarized light and left-handed circularly polarized light, and thereafter come into a second pair of bonded trapezoidal prisms (125) comprising third and fourth trapezoidal prisms, which has a similar structure to that of the first pair of bonded trapezoidal prisms (123), wherein the difference in height between the third and fourth trapezoidal prisms is half of the one between the first and second trapezoidal prisms. Therefore, when the laser beams have been passed through the second pair of bonded trapezoidal prisms (125), the beams having each of the two wavelengths are formed into eight beams which have a spacing "(⅛)W". Thereafter, when the eight beams having each wavelength have been passed through a quarter-wave plate (126), the eight beams are formed into alternate right-handed circularly polarized light and left-handed circularly polarized light.

The eight laser beams having each of the two wavelengths go ahead in a minus (−) z-direction in parallel to the front and rear of an x-direction (in FIG. 13), and are passed through a wavelengths-separating beams splitter (130). Thereafter, as shown in FIG. 11, eight beads arrayed in a bead-array on a substrate wherein each of DNA-samples (70) is disposed on each of the beads are simultaneously irradiated with the above beams through a tube lens (131) and an object lens (135). Eight of the DNA-samples (70) are irradiated with the eight laser beams having one of the two wavelengths as aligned in a y-direction as shown in FIG. 11, while other eight of the DNA-samples (70), which are aligned on a line (not shown in FIG. 11) as separated by m·P (wherein "m" represents an integer number, and "P" represents a pitch between lines) from the line of the first eight samples in an x-direction (in FIG. 11) are irradiated with the eight laser beams having the other of the two wavelengths. The tube lens (131) and the object lens (135) (in FIG. 13) form the reduced images of the two pinholes (1020) onto the samples (70) at ×1/M magnification. Thus, the diameter of each of the pinholes (1020) and the magnification "1/M" are set so that the diameter of each of spots can be approximately the same as the diameter "D" of each of the beads (in FIG. 11) or can be somewhat larger than the diameter "D".

A control device (8) in FIG. 13 controls an xy-stage (60) and the laser beams so that the laser beams can scan the xy-stage (60) in an x-direction (in FIG. 12A) as explained above with reference to FIGS. 12A and 12B. When the laser beams have traveled to samples on the edge of a bead- or dot-array, the laser beams are step-moved in a y-direction (in FIG. 12A), and each of the AO-modulators (1111 and 1210) is driven, whereby as shown in FIG. 12B, the multibeam with two-colors is synchronized with the travelling of the beads and travel in parallel therewith. A period of time required for the travelling by one pitch of the beams is almost used for irradiating the beads, and thus fluorescence is generated from a fluorescence-label on each of the beads during the above period of time. The generated fluorescence is passed through the object lens (135) and the tube lens (131) (in FIG. 13), reflected from the wavelengths-selecting beams splitter (130), passed through the window (151) of a fluorescence detection optical system (150), passed through a convex lens (152), a douser (153) with an orifice, and a lens (154), and thereafter the light path is branched by means of a wavelengths-selecting beams splitter (155), whereby the fluorescent images of the irradiated beads are formed in multichannel photo-multipliers (501 and 502). A fluorescent light with a wavelength of approximately 510 nm which has been excited with an exciting laser having a wavelength of 488 nm transmits through the wavelengths-selecting beams splitter (155) and is led to the multichannel photo-multiplier (501), while a fluorescent light with a wavelength of approximately 570 nm, which has been excited with an exciting laser having a wavelength of 532 nm is reflected from the wavelengths-selecting beams splitter (155) and is led to the multichannel photo-multiplier (502).

Each of the multichannel photo-multipliers (501 and 502) is followed by an interference filter (not shown) which transmits merely the components having fluorescent wavelengths mentioned above, which cuts extra noise lights. Furthermore, a pinhole array (not shown) which transmits merely eight fluorescent spots may be disposed between the interference filter and each of the photo-multipliers (501 and 502) so that noise lights such as fluorescence as generated from sites except the ones shown in FIG. 13 can not come into each channel of the photo-multipliers (501 and 502). Besides, detection with a higher SN ratio can be achieved by carrying out confocal detection.

When the window (151) (in FIG. 13) is formed to function as a color filter capable of cutting lights having wavelengths distant from a fluorescent wavelength, stray lights which act as outside noises can be shielded. Furthermore, a lens system comprising the tube lens (131) and the object lens (135) is of a double telecentric optical system, and thus major beams of fluorescence as emitted from each of the beads. Resultantly, even when a bright light comes into the fluorescence detection optical system (150) from the window (151) as a color filter, the bright light is almost shielded by disposing the douser (153) at the position of focus of the convex lens (152).

Although the reference numeral "155" is explained to be a uniform wavelengths-selecting beams splitter, the numeral "155" may be a pair of wavelengths-selecting beams splitters different in characteristics from each other, whose boundary is just an intermediate position between two beams of fluorescence at the front and rear of an x-direction (in FIG. 13). That is to say, since in a zone near a position wherein the two fluorescent images of each of the samples are formed, both images are completely separated, the pair of wavelengths-selecting beams splitters which is optimal to each fluorescent color can be disposed at the front and rear of an x-direction.

Eight fluorescent images of eight of the samples corresponding to each fluorescent wavelength are detected by means of eight channels of the photo-multiplier (501 or 502), respectively. A period of time required for detecting a bead is $P/V_s(=\Delta t)$, and the number of count of photon pulses coming into the photo-multiplier (501 or 502) is counted by the control device (8). The number of the counted photon pulses is stored every address of a bead, or every color of fluorescence in memory in a control circuit.

Data as stored in this memory may be compared with other data which have been separately stored, whereby the state of a DNA with fluorescence detected can be inspected and assayed.

Incidentally, information upon the number of photon pulses count as obtained above may be indicated on a display (not shown), together with information upon the address of a bead which a sample is disposed on so that an operator can access thereto.

Furthermore, information upon the number of photon pulses count as obtained above may be transmitted to an analysis system, an analytical instrument and/or other inspection device, or the like through a means of communication, together with information upon the address of a bead disposed on a sabstrate so that such information can be used.

Some samples disposed on beads include great many of fluorescent molecules. In such a case, excessive photon pulses come into the photo-multiplier (501 or 502) during a period of time of $\Delta t$. Letting this number be "$N_p$", and letting the time width of a photon pulse be "$\Delta t_p$", when $N_p > \Delta t/\Delta t_p$, photon pulses are superposed, and thus it is difficult to count the photon pulses. For samples which emit fluorescent lights of from extremely weak intensity to very strong intensity, signals as transmitted from the control circuit to the AO-modulators are controlled as follows so as to solve the problem mentioned above.

That is to say, a period of time "Δt" required for detecting one bead is divided into two parts; and the amplitude of a high-frequency wave in the AO-modulators is changed so that the bead can be irradiated, for example, with about 100% of the exciting light during Δt/2 of the first half period, and with several % of the exciting light during Δt/2 of the last half period. In such a manner, the precise detection of fluorescence can be achieved in a wider dynamic-range from samples with very small fluorescent molecules to samples with great many fluorescent molecules. In addition, once scanning permits two fluorescence-labels to be detected in a wider dynamic-range.

Figure 17:
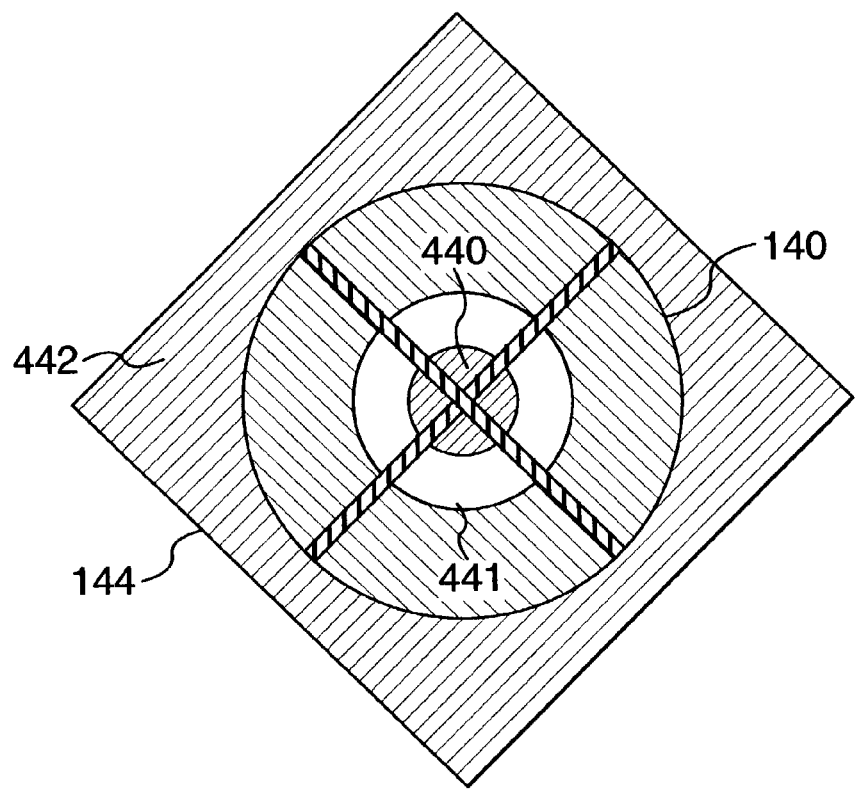
FIG. 17 is a plan view illustrating a quadrant sensor for detecting a reflected light from a bead in the present invention.

The reference numeral "134" in FIG. 13 represents a beam splitter which reflects an exciting light with low reflectance. The exciting light reflected from the beam splitter (134) comes into a lens (141). The lens (141) forms the image of the pupil of the object lens onto the sensor surface of a quadrant position sensor (140) which is followed by a mask (144) whose detailed drawing is shown in FIG. 17.

Figure 14:
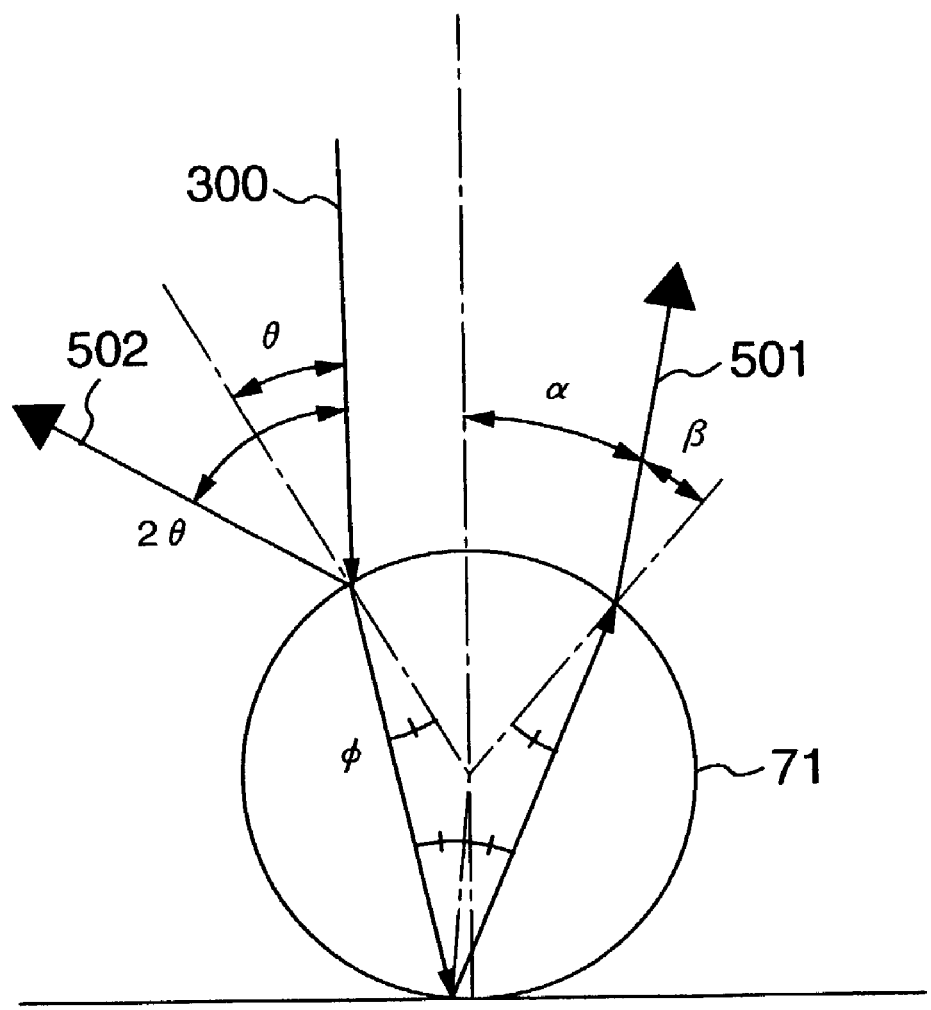
FIG. 14 is a sectional view of a bead, which illustrates a relationship between an exciting light which the bead is irradiated with and a reflected light in the present invention.

As mentioned above with reference to FIG. 13, eight beams of a multispot-beam come into a tube lens in parallel to the optical axis of the tube lens, and are focused upon the pupil center of an object lens. As shown in FIG. 14, a bead (71) is irradiated perpendicular to the surface of the bead-array with each (300) of the eight beams as transmitted the object lens. Light (502) as reflected from the surface of the bead is shifted from the center of the bead, and thus an incident angle "θ" is provided, and then the reflected light is reflected with a large angle "2θ" between the perpendicular line and the reflected light, whereby the reflected light does not come into the object lens.

On the other hand, an exciting light which has refracted on the surface of the bead and come into the bead is reflected from the under surface of the bead, and refracted on the top surface of the bead, and then upward emitted with the angle "α" between the optical axis and the emitted light. Even when this reflected light is considerably deviated from the center of the bead, as shown by the reference numeral "3001A" in FIG. 15, when the reflected light returns to the object lens, the angle "α" between the optical axis and the reflected light is small, whereby the reflected light almost comes into the object lens.

In the position of the pupil of the object lens, the position of light as returned from the bead depends upon an angle between the returned light and the optical axis of a light emanating from the bead. Thus when the angle therebetween is smaller than the angle "$\theta_{NA}(=\sin^{-1}_{NA})$" corresponding to the NA of the object lens, the returned light is passed through the object lens, while the angle therebetween is larger than the angle "$\theta_{NA}(=\sin^{-1}_{NA})$", the returned light is not passed therethrough. As shown in FIG. 16, only lights coming into a white area (or a blank section) in the pupil, that is to say, an area except radial sections from the center "O" of the pupil to the line "A", and from the line "B" to the line "C", shall be detected. Lights which are passed through this white area and reflected from the spherical surface of the bead are the lights (3002) coming into the circular portion (3002A) in FIG. 15, while lights which are passed through this white area and refracted at the bead and returned are the lights (3001) coming into the circular portion (3001A) in FIG. 15.

Figure 15:
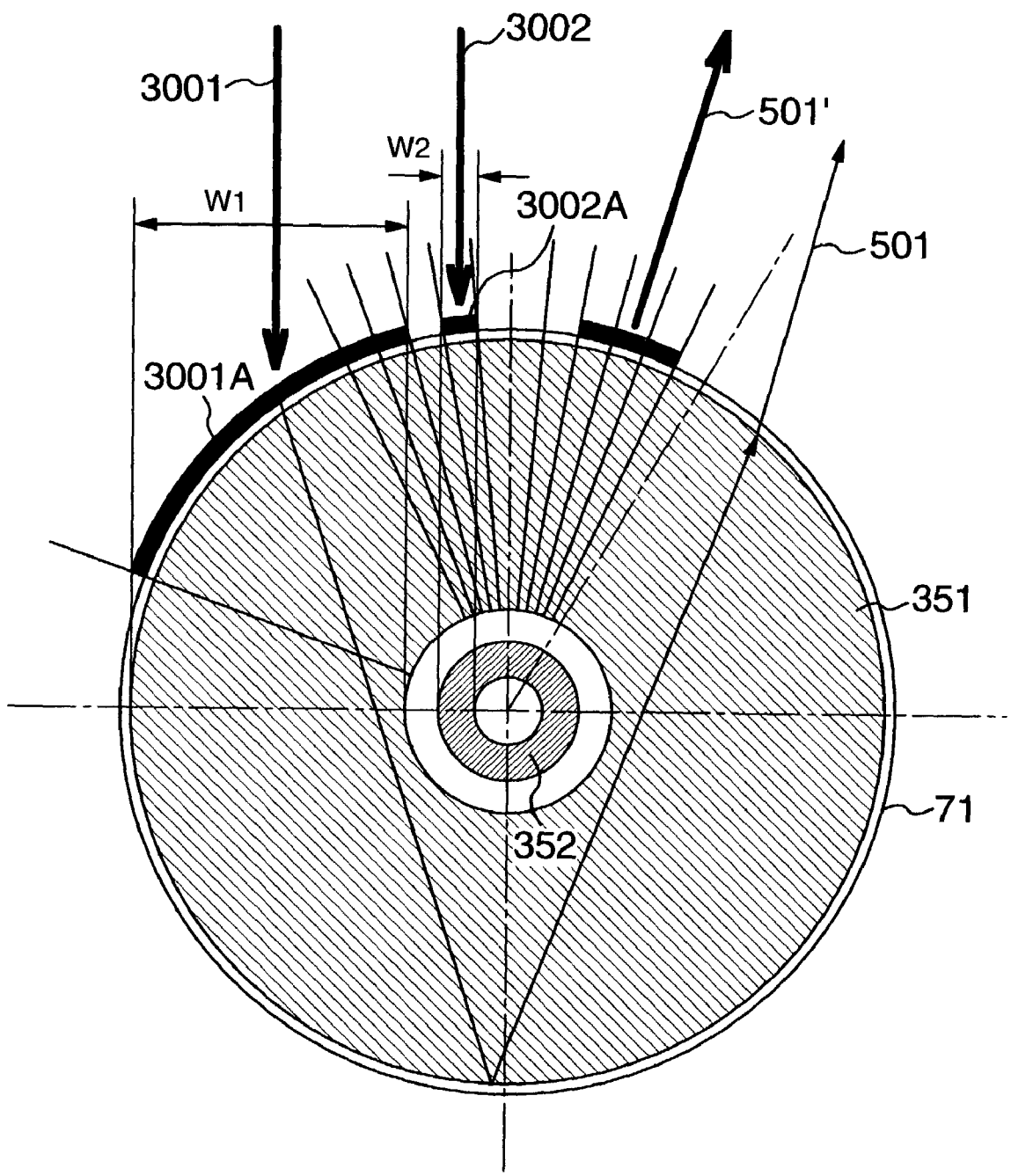
FIG. 15 is another sectional view of a bead, which illustrates a relationship between an exciting light which the bead is irradiated with and a reflected light in the present invention.
Figure 16:
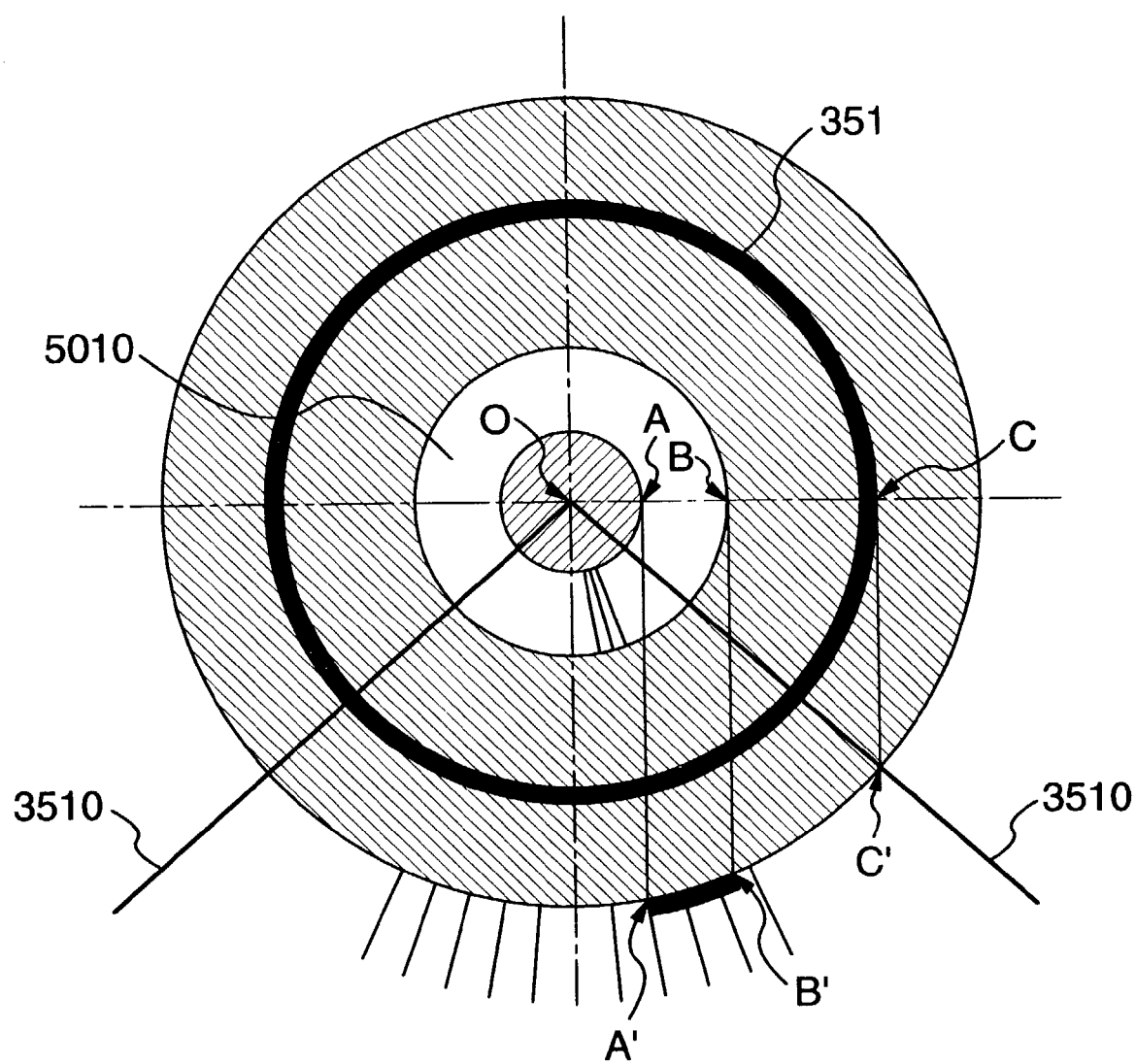
FIG. 16 is a plan view illustrating the state of a reflected light on the pupil of an object lens in the present invention.

When the lights (501') as refracted at the bead and returned in FIG. 15 come into the circular portion, lights from a broad area as indicated by the arrow "W1" are returned into the white area in the pupil as shown in FIG. 16.

On the other hand, lights as reflected from the surface of the bead come into the circular portion, merely lights from a narrow area as indicated by the arrow "W2" are returned into the white area in the pupil as shown in FIG. 16. In addition, the lights as reflected from the surface of the bead are returned to the opposite side of the pupil to the side of the lights (501') as refracted and returned.

Figure 18:
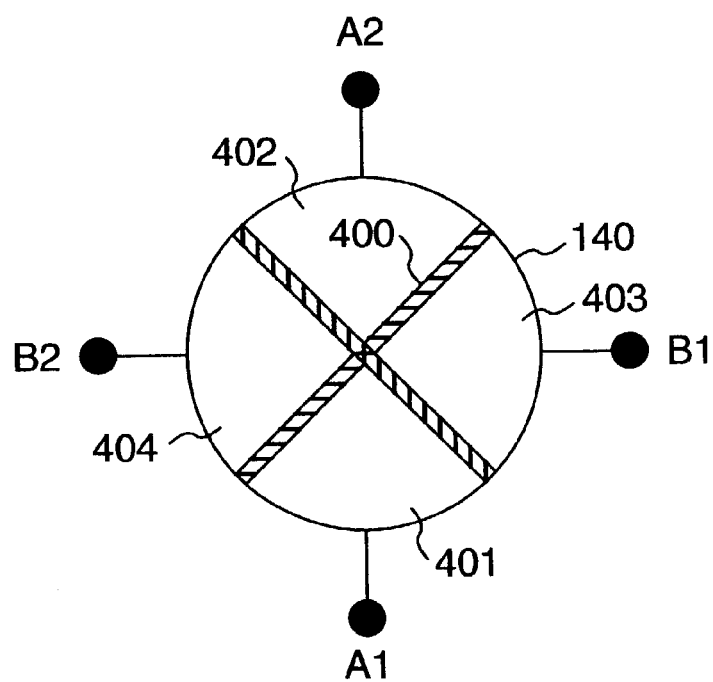
FIG. 18 is another plan view illustrating a quadrant sensor for detecting a reflected light from a bead in the present invention.

With the properties of the returned lights mentioned above, a mask (144) which comprises an area (441) corresponding to the white area in the pupil in FIG. 16 as a transmission area, and the other area as a shielding area shall be provided, as shown in FIG. 17, in the front of the quadrant position sensor (140) as disposed at a position to which the image of the pupil is formed as shown in FIG. 17. In the back of this mask (144), the quadrant position sensor (140) as shown in FIG. 18 is disposed. The quadrant position sensor (140) comprises four sensors (401, 402, 403 and 404) which are independent of one another and separated with a gap (400) from one another, wherein the upper terminal (A1) from the sensor (401) and the lower terminal (A2) from the sensor (402), and the right-hand terminal (B1) from the sensor (403) and the left-hand terminal (B2) from the sensor (404) are diagonally projected.

Figure 25:
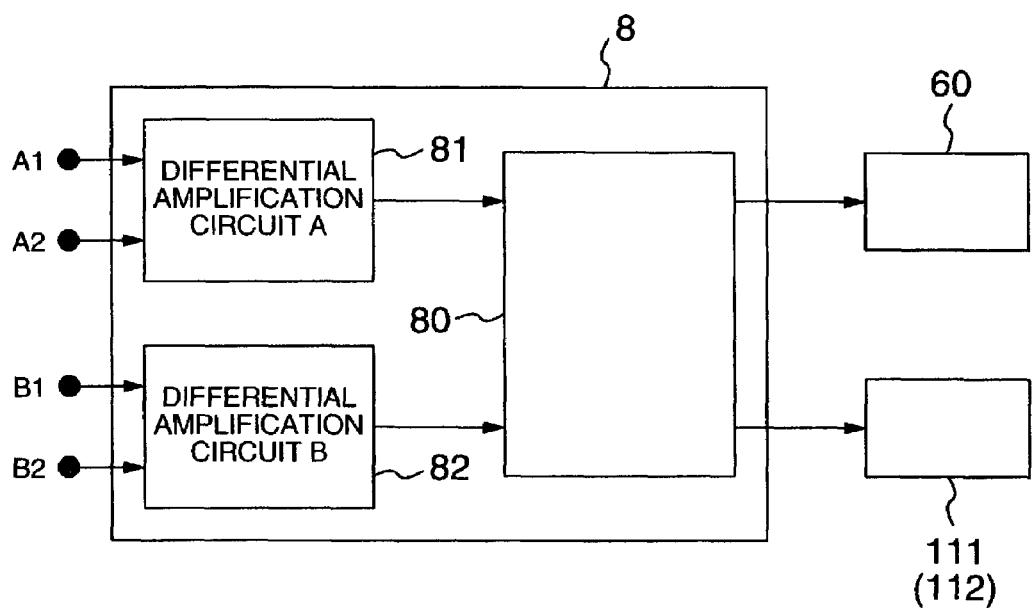
FIG. 25 is a block diagram of a circuit for treating signals received by a quadrant sensor in the present invention.

A direction indicated by the upper terminal (A1) and the lower terminal (A2) corresponds to the direction of an array of the exciting multispot, while a direction indicated by the right-hand terminal (B1) and the left-hand terminal (B2) corresponds to a direction perpendicular to the direction of the array. As explained with reference to FIGS. 14 to 16, if an exciting spot light is deviated in the direction of the array thereof from the center of a bead irradiated, a voltage between the terminals (A1) and (A2) is varied, and then the control device (8) as shown in FIG. 25 controls a differential amplification circuit A (81) to amplify the signal of the difference in voltage or sign, wherein a deviation signal of the exciting spot light in the direction of the array is AD-converted so as to be inputted into a control circuit (80). Similarly, the difference in voltage between the terminals (B1) and (B2) is amplified by means of a differential amplification circuit B (82), a deviation signal in a direction orthogonal to the AD-converted array is inputted into the control circuit (80).

When the deviations in the two directions are detected, a deviation in a direction orthogonal to the array as shown in FIG. 25 is corrected by shifting the frequency of a high-frequency signal as inputted into the AO-modulators (1111 and 1210) as shown in FIG. 13 by means of the control device (8) so that the deviation can be decreased, while a deviation in the direction of the array is corrected by controlling the y-stage of the xy-stage (60) in FIG. 13 by means of the control device (8).

Figure 19:
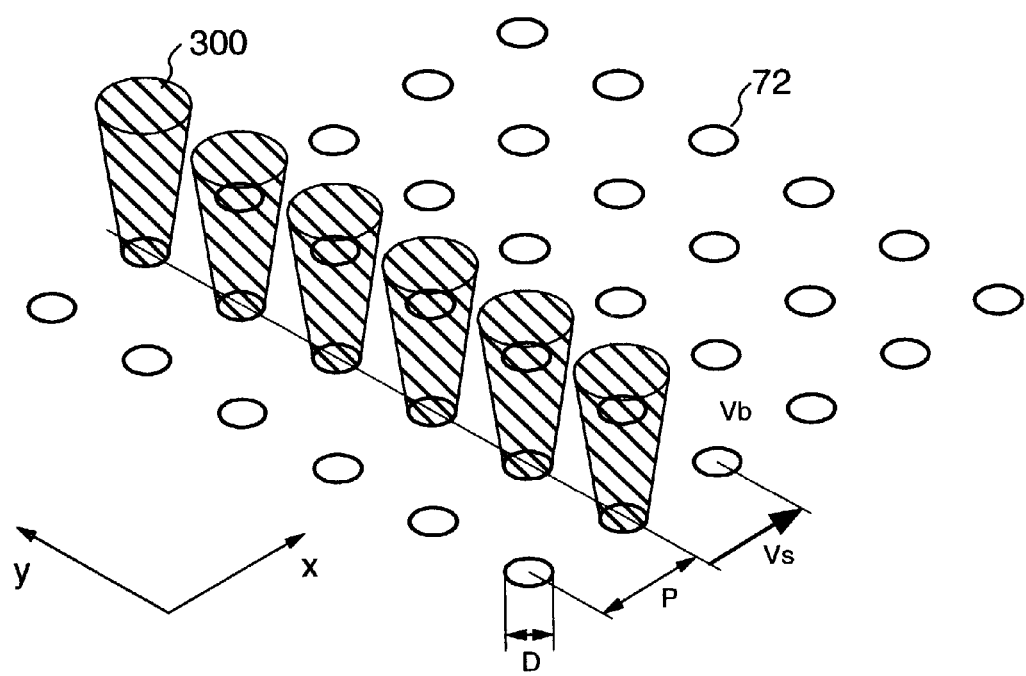
FIG. 19 is a perspective view of samples on a bead-array, which illustrates the state of detecting a dot-array wherein samples may include a fluorescent material according to the present invention.
Figure 20:
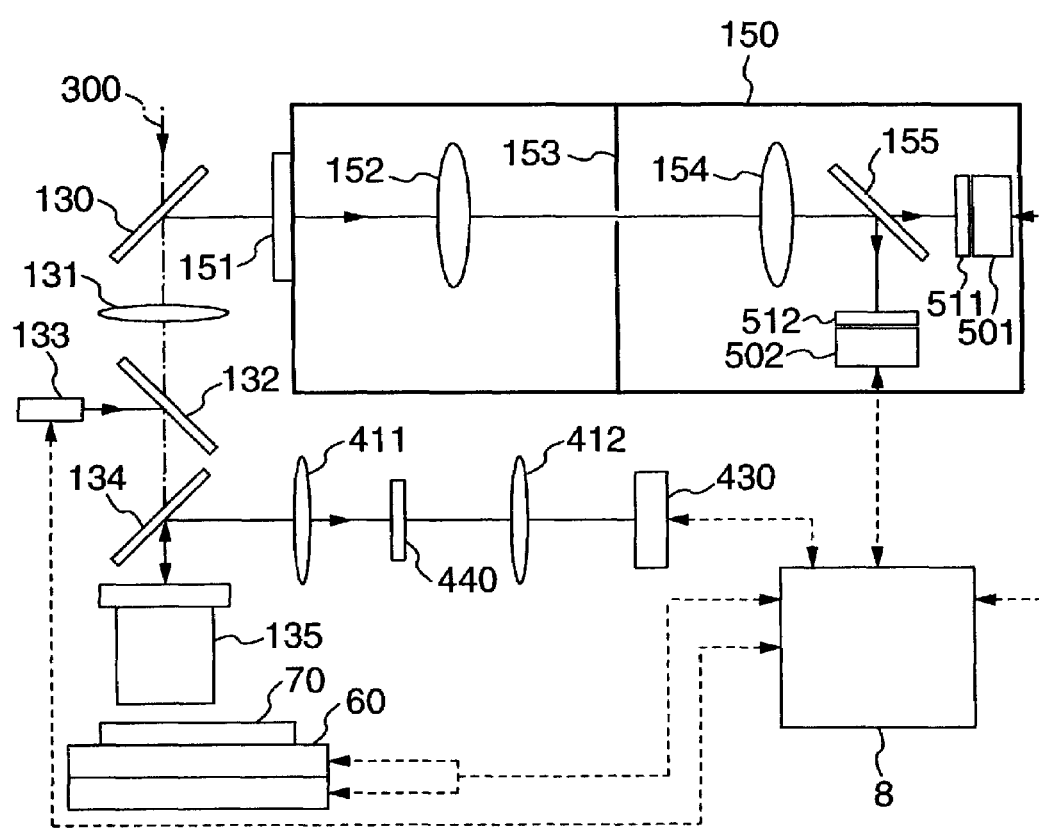
FIG. 20 is a schematic front view illustrating the constitution of an apparatus for detecting a dot-array wherein samples may include a fluorescent material according to the present invention.

FIG. 19 illustrates a working example of a fluorescent-label dot-array inspection apparatus of the present invention, wherein the reference numeral "72" represents DNA dots as dotted by means of a spotter or an ink-jet printer. The diameter of a dot is dozens of microns, and such dots are arrayed in square pitch with a pitch "P" several times the diameter of a dot. An excitation optical system wherein these some dots can be simultaneously irradiated is approximately the same as the one illustrated in FIG. 11. However, the present excitation optical system is designed in the manner wherein the diameter of a beam for irradiation is dozens of microns since the diameter of a dot is larger than that of a bead. FIG. 20 illustrates an optical system wherein the multi-exciting spot forming optical system is omitted. Dot-arrays on the substrate are simultaneously irradiated with a multispot-exciting light (300) having q (wherein q is an integer, q≧2) of spots. For example, fluorescence as generated with the exciting light is treated in a similar manner to the one shown in FIG. 11 so that a two-wavelengths fluorescent light corresponding to a two-wavelengths exciting light can be detected by means of a fluorescence-detecting system (150).

Hereinafter, the positional relationship between samples and an exciting multispot in the present working example will be explained with reference to FIG. 27. Incidentally, the detection of a bead-array as shown in FIG. 26 also is operated with a positional relationship similar thereto, which will be explained later.

Figure 27A:
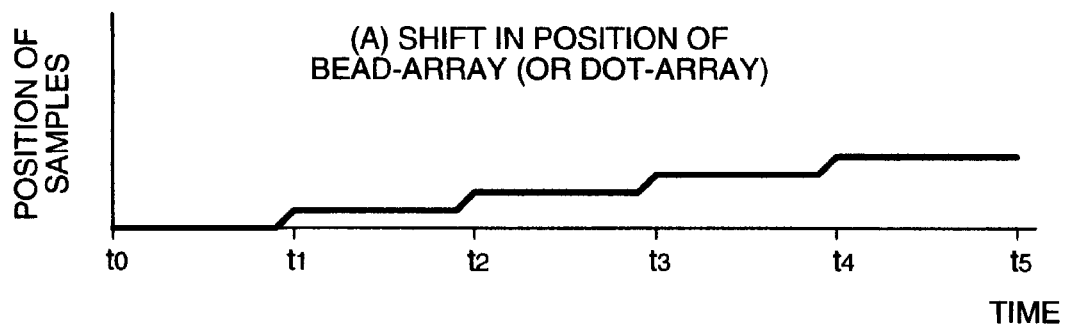
FIG. 27A is a graph illustrating a shift in the position of the bead-array in the present invention.
Figure 27B:
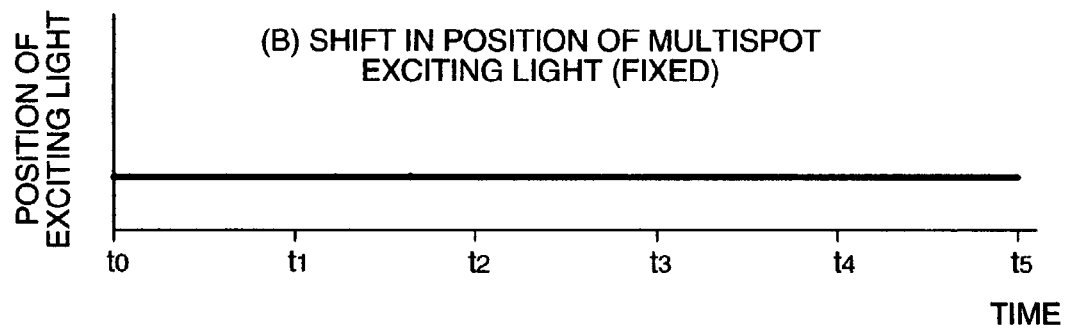
FIG. 27B is a graph illustrating a shift in the position of multispot exciting lights in the present invention.

FIG. 27A demonstrates the time variation of the position of a sample in a bead- or dot-array; and FIG. 27B demonstrates the time variation of the position of an exciting light. A stage is stepwise moved by a length corresponding to the array pitch "P", of the bead- or dot-array, and the detection is carried out within a period of time slightly shorter than $\Delta t(=t_{n+1}-t_n)$. Accordingly, the exciting light is substantially standing as shown in FIG. 27B.

Figure 26:
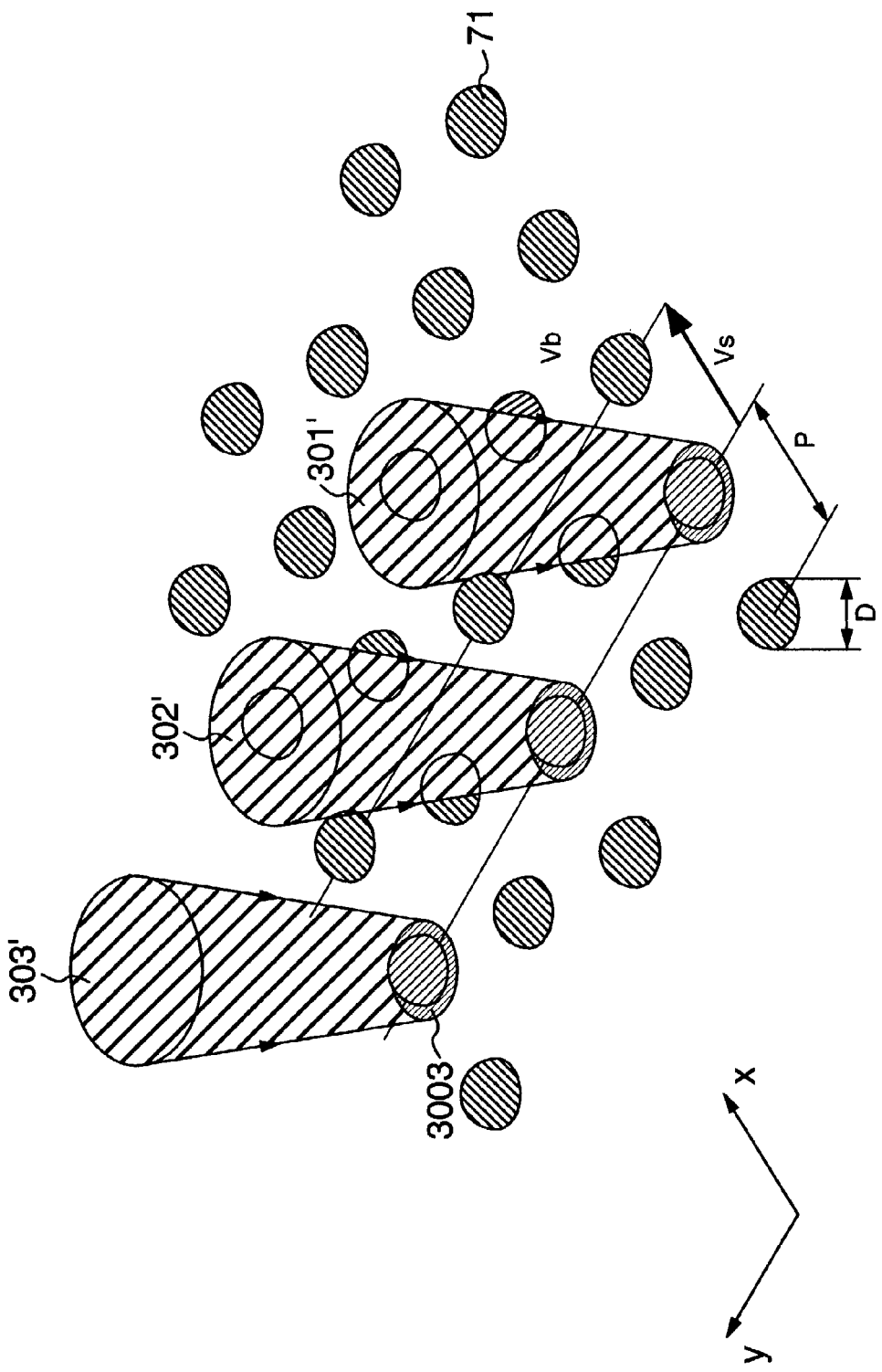
FIG. 26 is a perspective view of samples on a bead-array, which illustrates the state of detecting a bead-array wherein samples may include a fluorescent material according to the present invention.

When beads as shown in FIG. 26 are detected, a light reflected from each of the beads as hereinbefore explained in FIG. 1 is detected by means of a quadrant positional sensor which is disposed at a position conjugated with the pupil of an object lens, whereby it can be detected whether the center of the bead is corresponding to the center of the exciting light spot. If the center of the bead is deviated from the center of the exciting light spot, the exciting light spot is controlled.

Figure 21:
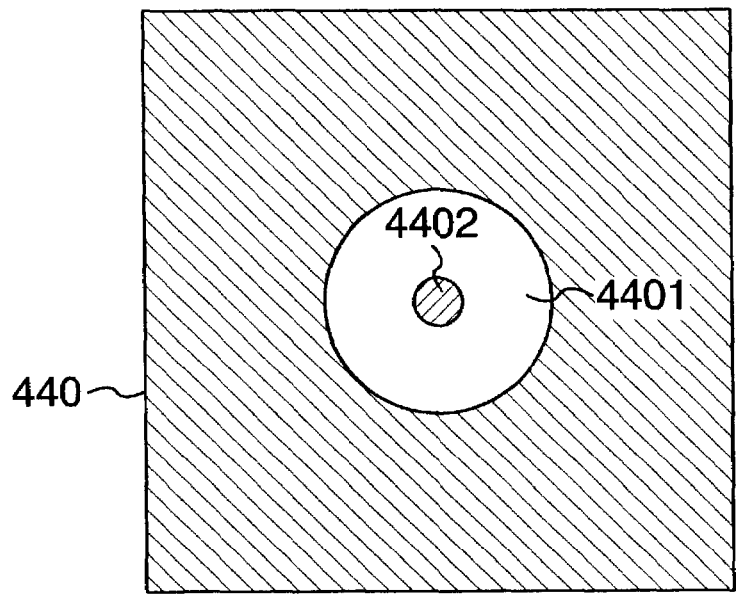
FIG. 21 is a plan view illustrating a zero-point light cutoff filter in the present invention.

When dots in the dot-array as shown in FIG. 19 are detected, the deviation in position of an exciting light and a dot is detected by using the optical system as shown in FIG. 20, and if necessary, the deviation is corrected. Hereinafter, the present working example will be in detail explained with reference to FIG. 20. In FIG. 20, a half mirror (134) reflects a part of an exciting light as reflected from a dot of a sample, and leads to a lens (411). The reference numeral "440" represents a zero-dimensional cutoff filter, whose detailed drawing is shown in FIG. 21, wherein the zero-dimension of a light reflected from a sample is shielded by means of a portion (4402) in FIG. 21. That is to say, the zero-dimensional cutoff filter is disposed at a position at which the image of the pupil of the object lens (135) is formed by the lens (411). The regular reflection light of the exciting light as reflected from a sample is shielded by the portion (4402) of the filter, whereby only a diffracted light is passed through the portion (4401) of the filter.

Each of dots in a dot-array is provided by dotting a liquid comprising a probe-DNA and a solvent by means of a spotter or an ink-jetting machine, and thereafter hybridizing a fluorescence-labeled target-DNA. Therefore, the dotted portion is protuberant as compared to the peripheral glass substrate. Thus, when a dot is irradiated with each laser, the laser is diffracted at this protuberant portion, and the reflected light is diffracted in a direction different from the zero-dimensional light. Consequently, only this diffracted light is passed through the portion (4401) of the zero-dimensional light cutoff filter (440).

Figure 22:
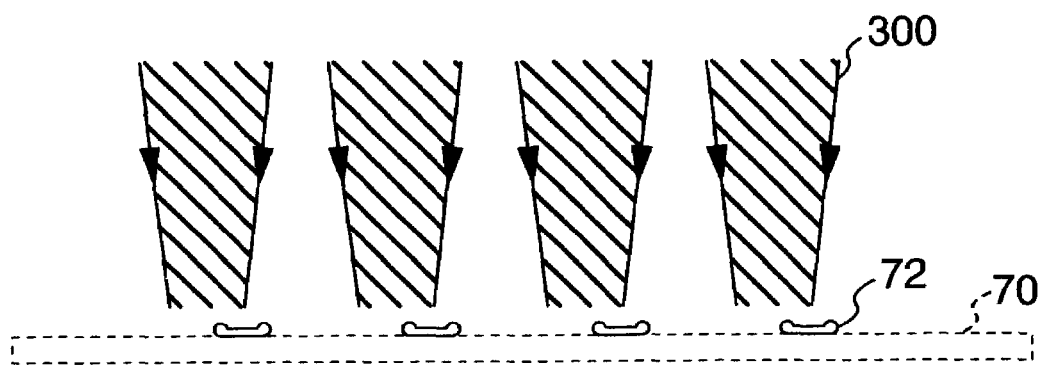
FIG. 22 is a front sectional view of samples on a bead-array wherein the samples are irradiated with a multispot exciting lights deviated in the present invention.
Figure 23:
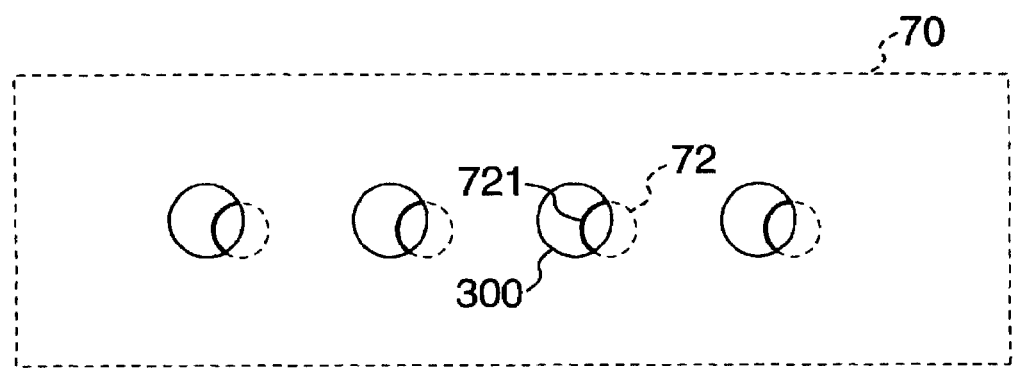
FIG. 23 is a plan view of the samples on a bead-array wherein the samples are irradiated with a multispot exciting lights deviated in the present invention.
Figure 24:
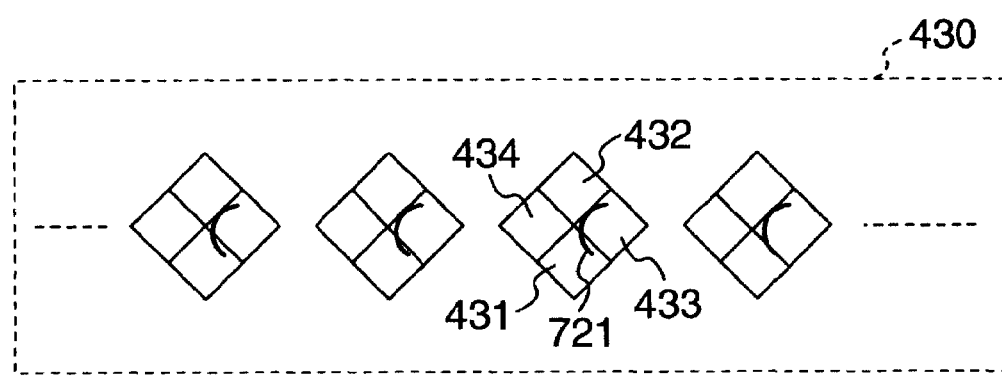
FIG. 24 is a plan view of a quadrant sensor array, which illustrates the state of images of exciting lights which have transmitted a zero-point light cutoff filter and projected on a quadrant sensor in the present invention.

FIG. 22 illustrates the state of samples (72) in a dot-array being irradiated with a multispot light (300) deviated. When the samples are irradiated in such a state of deviation, the light which has been reflected and passed through the zero-dimensional light cutoff filter (440) forms on an imaging sensor an image wherein the edge of the dot is bright and the other portion is dark as shown in FIG. 23, by the lens (412) as shown in FIG. 20. Thus as imaging sensors, for example, quadrant sensors as shown in FIG. 24 are previously disposed at a pitch equal to the array pitch of the zero-dimensional light cutoff filter transmission images (721) of the dots. In addition, the quadrant sensor is disposed in such a manner that if the exciting light corresponds to the dot, the center of the quadrant sensor corresponds to the center of the image.

Accordingly, when the exciting light is deviated from the dot as shown in FIG. 22, the zero-dimensional light cutoff filter transmission images (721) is formed out of the center of the quadrant sensor as shown in FIG. 24, whereby, the intensity of detection is strong in the order of the quadrant sensors (433), (431), while the quadrant sensors (432) and (434) do not substantially receive light. As a result, by using a differential amplifier in FIG. 25 as explained hereinbefore, the two-dimensional direction of the deviation can be taken, and thus the stage (60) is finely controlled through the control device (8) so that the deviation can be corrected and a correct position can be irradiated with the exciting light.

As explained in detailed, according to the present invention, only an area to be detected in each of DNA samples which may include a fluorescent material or a fluorescent label and is disposed on a bead- or dot-array can be irradiated with an exciting light so as to detecting fluorescence, whereby the high-sensitive, wider dynamic-range and high-speed detection can be achieved. As a result, the present invention is remarkably effective for even a high-precision and high-speed inspection in the field wherein a large amount of samples are treated for a future medical inspection and the like.

The present invention may be embodied in other specific forms without departing from the spirit or essential characterized thereof. Therefore the present embodiments should be considered to be illustrative but not to be limited to in all respects. Furthermore, the scope of the invention should be indicated by appended claims rather than by the foregoing descriptions. Therefore, all changes and modifications which fall within the meaning and range of equivalency of claims are intended to be embraced in the present invention.

What is claimed is:

1. A method of obtaining fluorescent images of samples of fluorescent material, comprising the steps of:
   (a) moving a substrate in a first direction, said substrate comprising a an array of compartments for carrying said samples, each row in the array of compartments being seperated by an equal pitch distance;
   (b) sequentially irradiating said compartments in said array of compartments with an exciting light while moving said substrate in said first direction by scanning said exciting light over said pitch distance at substantially the same speed as the moving substrate, including varying an intensity of said exciting light from a first irradiating value to a second irradiating value during the period of time that one compartment is scanned;
   (c) detecting fluorescent light generated from each of said samples due to irradiation by said exciting light while cutting off light reflected from said substrate due to the scanning of said exciting light; and
   (d) determining a value of fluorescence as generated from each of said samples based upon information from said fluorescent light detected in step (c).

2. A method of obtaining fluorescent images according to claim 1, wherein said exciting light consists of two or more beams, with which said plurality of compartments is simultaneously irradiated.

3. A method of obtaining fluorescent images according to claim 1, wherein said determining step (d) includes obtaining signals for each of said samples from fluorescence detection as provided by the detecting step (c) so as to produce detection results corresponding to the varied intensity of said exciting light.

4. A method of obtaining fluorescent images of samples which may include a fluorescent material, comprising steps of:
   (A) moving a substrate in a first direction, said substrate comprising an array of compartments, each row in the array of compartments being separated by an equal pitch distance and each compartment disposed with a sample;
   (B) sequentially irradiating said samples with an exciting light while moving said substrate by scanning the exciting light in said first direction over said pitch distance at substantially the same speed as th moving substrate, wherein an intensity of said exciting light is changed from a first irradiating value to a second irradiating value within a period of time during which each sample is irradiated;
   (C) obtaining fluorescent images of each of said samples by detecting fluorescent lights generated from each of said samples due to the sequential irradiation of said samples by the exciting light performed in said irradiating step (B) while cutting off exciting light reflected from said substrate; and
   (D) processing said fluorescent images of each of said samples as obtained in said obtaining step (C) so as to determine a true value of fluorescence as generated from each of said samples.

5. A method of obtaining fluorescent images according to claim 4, wherein said moving step (A) includes arranging said plurality of compartments into a plurality of rows on said substrate; and said irradiating step (B) includes simultaneously irradiating two or more samples in a row of said compartments and sequentially irradiating each row in said plurality of rows wherein each of said two or more samples is irradiated with one or more exciting lights; and said obtaining step (C) includes simultaneously obtaining images of said samples as said compartments are irradiated with said exciting light.

6. A method of obtaining fluorescent images according to claim 4, wherein said irradiating step (B) includes irradiating each of said samples with two or more exciting lights different in intensity from one another; and said obtaining step (C) includes obtaining two or more images of each of said samples with two or more fluorescent lights different in intensity from one another as generated from each of said samples.

7. A method of obtaining fluorescent images according to claim 4, wherein a dynamic range of said true value of fluorescence as determined in said treating step (D) is larger than 1000 counts per unit of time.

8. A method of inspecting DNA, comprising the steps of:
   (a) moving a substrate in a first direction, the substrate containing a plurality of DNA-samples arranged in an array of rows separated by an equal pitch distance, wherein each DNA-sample is labeled with a fluorescence and each DNA-sample is disposed on a bead;
   (b) sequentially irradiating each of p DNA-samples in sad plurality of DNA-samples with q exciting lights by scanning said exciting lights over said pitch distance at substantially the same steed as the moving substrate, wherein $p \geq 2$;
   (c) switching each of said exciting lights into r beams different in intensity from one another within a scanning period during which each of said DNA-samples is irradiated, wherein $r \geq 2$;
   (d) detecting r fluorescent lights as generated from each of said DNA-samples in said irradiating step (a), corresponding to said beams while cutting off light reflected from said substrate due to irradiation of said substrate by said q exciting lights;
   (e) inspecting a DNA in each of said DNA-samples by using information upon said r fluorescent lights each different in intensity from one another as detected in said detecting step (b).

9. A method according to claim 8, wherein $p \geq q \geq 2$; and said irradiating step (c) includes simultaneously irradiating s of said p DNA-samples with said q exciting lights during each scanning period.

10. A method of inspecting DNAs according to claim 8, wherein each of said p DNA-samples is attached to the surface of said beads.

11. A method of inspecting DNA, comprising the steps of:
   (a) moving a substrate in a first direction, the substrate containing a plurality of DNA-samples arrange an array of rows separated by an equal pitch distance, wherein each DNA-sample is labeled with a fluorescence and and each DNA-sample is disposed on a bead;
   (b) sequentially irradiating each of p DNA-samples in said plurality of DNA-samples with q exciting lights by scanning said q exciting lights over said pitch distance at substantially the same speed as the moving substrate, wherein $p \geq 2$;
   (c) switching each of said q exciting lights into two beams different in intensity from each other within a scannig period during which each of said DNA-samples is irradiated;
   (d) converging two fluorescent lights as generated from each of said DNA-samples in said irradiating step (b), corresponding to said two beams different in intensity from each other while cutting off light reflected from said substrate due to irradiation of said substrate by said exciting lights;
   (e) branching said two fluorescent lights as converged in said converging step (d) into two fluorescent lights different in intensity from each other so as to detect each of said branched two fluorescent lights; and
   (f) inspecting a DNA in each of said DNA-samples by using information upon each of said two fluorescent lights as detected in said detecting step (e).

12. A method of inspecting DNA according to claim 11, wherein $p \geq q \geq 2$; and said irradiating step (c) includes an operation of simultaneously irradiating q of said DNA-samples with said q exciting lights during each scanning period.

13. A method of inspecting DNA according to claim 11, wherein the dynamic range of a fluorescence image of each of said DNA-samples is 1000 counts per unit of time or more.

14. A method of inspecting DNA according to claim 11, wherein each of said DNA-samples is attached to the surface of said beads.

15. A method of inspecting DNA, comprising the steps of:
   (a) continuously moving, in one direction, p DNA-samples labeled with a fluorescence, each DNA-sample disposed on the surface of an array of beads or dots arranged at a fixed pitch on a substrate, wherein $p \geq 2$;
   (b) sequentially irradiating each of said beads or dots with one spot of a spot exciting-light comprising one or more spots, each of said one or more spots of said spot exciting-light having a beam diameter approximately equal to a diameter of said beads or dots, wherein said beads or dots are moved in one direction and are irradiated with said spots of said spot exciting-light and said spot exciting-light moves in said one direction at substantially the same speed as said beads or dots so that said spot exciting-light tracks said beads or dots, wherein each of said beads or dots is irradiated by a period of time substantially equal to the time required for moving said spots of said spot exciting-light by said fixed pitch, and wherein each spot of said spot exciting-light changes intensity from a first irradiating value to a second irradiating value within said period of time during which said beads are irradiated;

(c) separating fluorescence as generated from each of said DNA-samples from said spot exciting-light so as to detect said fluorescence while cutting off light reflected from said substrate due to irradiation of said substrate by said spot of exciting-light; and (d) inspecting said DNA samples by using information as obtained in said detecting step (c).

16. A method of inspecting DNA according to claim 15, wherein said beads or dots are two-dimensionally arrayed; and said spot exciting-light comprises at least two spots.

17. A method of inspecting DNA according to claim 15, wherein the operation wherein said spot exciting-light tracks said beads or dots is carried out by synchronizing said spot exciting-light with continuous movement of said DNA-samples into one direction by means of a light deflector.

18. A method of inspecting DNAs according to claim 15, wherein said detecting step (c) is carried out according to a photon counting detection method.

* * * * *